United States Patent
Van Den Brink et al.

(10) Patent No.: US 10,982,204 B2
(45) Date of Patent: *Apr. 20, 2021

(54) VARIANTS OF CHYMOSIN WITH IMPROVED MILK-CLOTTING PROPERTIES

(71) Applicant: Chr. Hansen A/S, Hoersholm (DK)

(72) Inventors: Johannes Maarten Van Den Brink, Herlev (DK); Jesper Langholm Jensen, Copenhagen Ø (DK); Jonas Jacobsen, Copenhagen Ø (DK); Martin Lund, Copenhagen Ø (DK); Iben Jeppesen, Alleroed (DK); Christian Jaeckel, Vaerloese (DK)

(73) Assignee: CHR. HANSEN A/S, Hoersholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/121,286

(22) PCT Filed: Feb. 26, 2015

(86) PCT No.: PCT/EP2015/054020
§ 371 (c)(1),
(2) Date: Aug. 24, 2016

(87) PCT Pub. No.: WO2015/128417
PCT Pub. Date: Sep. 3, 2015

(65) Prior Publication Data
US 2017/0067041 A1 Mar. 9, 2017

(30) Foreign Application Priority Data

Feb. 26, 2014 (EP) ..................................... 14156707
Jul. 11, 2014 (EP) ..................................... 14176664

(51) Int. Cl.
C12N 9/48 (2006.01)
C12N 9/64 (2006.01)
A23C 19/04 (2006.01)

(52) U.S. Cl.
CPC ............ *C12N 9/6483* (2013.01); *A23C 19/04* (2013.01); *C12Y 304/23004* (2013.01)

(58) Field of Classification Search
CPC ................................................... C12N 9/6483
See application file for complete search history.

(56) References Cited

U.S. PATENT DOCUMENTS 7,390,936 B1 * 6/2008 Van Rooijen ............ C12N 9/50
435/468
7,482,148 B2 * 1/2009 Mule .................... C12N 9/6483
435/226

(Continued)

FOREIGN PATENT DOCUMENTS

EP 0 123 928 A2 11/1984
JP 2010-046034 A 3/2010

(Continued)

OTHER PUBLICATIONS

Pungercar. Complete primary structure of lamb preprochymosin deduced from cDNA. Nucleic Acids Res. Aug. 11, 1990;18(15):4602.*

(Continued)

*Primary Examiner* — Yong D Pak
(74) *Attorney, Agent, or Firm* — Foley & Lardner LLP

(57) ABSTRACT

Variants of chymosin with improved milk-clotting properties.

Figure 2:
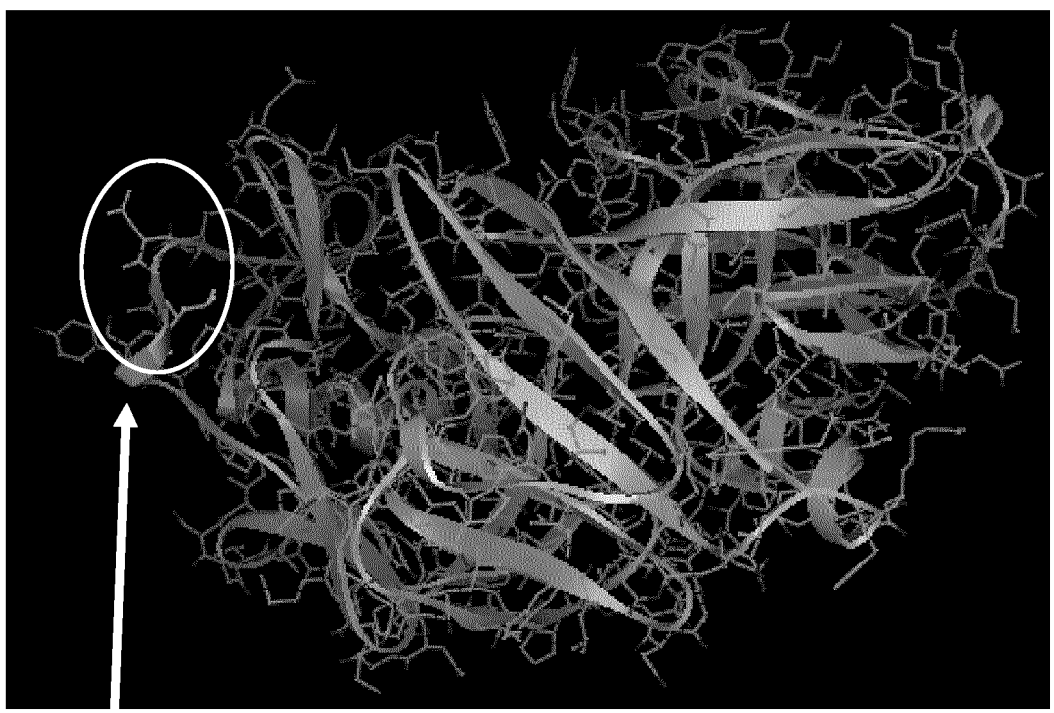

7 Claims, 4 Drawing Sheets
Specification includes a Sequence Listing.

(56) References Cited

U.S. PATENT DOCUMENTS

| | | | |
|---|---|---|---|
| 9,822,352 B2* | 11/2017 | Dekker | C12Y 304/23004 |
| 9,930,899 B2* | 4/2018 | Van Den Brink | A23C 9/1209 |
| 10,167,463 B2* | 1/2019 | Dekker | C12Y 304/23004 |
| 2008/0226768 A1 | 9/2008 | Kappeler et al. | |
| 2011/0287137 A1 | 11/2011 | Kappeler et al. | |
| 2015/0140169 A1 | 5/2015 | Dekker et al. | |
| 2015/0173383 A1 | 6/2015 | Van Den Brink et al. | |
| 2018/0110234 A1 | 4/2018 | Faiveley et al. | |
| 2018/0187179 A1 | 7/2018 | Jaeckel et al. | |
| 2018/0251747 A1 | 9/2018 | Jaeckel et al. | |
| 2018/0317510 A1 | 10/2018 | Van Den Brink et al. | |
| 2019/0116821 A1 | 4/2019 | Jaeckel et al. | |
| 2019/0174783 A1 | 6/2019 | Jaeckel et al. | |

FOREIGN PATENT DOCUMENTS

| | | | |
|---|---|---|---|
| JP | 2010-099082 A | 5/2010 | |
| JP | 2011-182794 A | 9/2011 | |
| RU | 2 192 137 C2 | 11/2002 | |
| WO | WO 02/36752 A2 | 5/2002 | |
| WO | WO 2004/031733 A2 | 4/2004 | |
| WO | WO 2005/003345 A2 | 1/2005 | |
| WO | WO 2008/098973 A1 | 8/2008 | |
| WO | WO 2010/110464 A1 | 9/2010 | |
| WO | WO 2013/164479 A2 | 11/2013 | |
| WO | WO 2013/164481 | * | 11/2013 |
| WO | WO 2013/164481 A1 | 11/2013 | |
| WO | WO 2013/174840 A1 | 11/2013 | |
| WO | WO 2015/128417 A1 | 9/2015 | |
| WO | WO 2016/207214 A1 | 12/2016 | |
| WO | WO 2017-037092 A1 | 3/2017 | |

OTHER PUBLICATIONS

Branden et al. Introduction to Protein Structure, Garland Publishing Inc., New York, p. 247, 1991.*

Lindblad-Toh. Genome sequence, comparative analysis and haplotype structure of the domestic dog. Nature 438:803-819(2005).*

E2R9E5_CANLF. UnitProtKB Database. 2014.*

Sambrook et al. Molecular Cloning, 1989, Cold Spring Harbor Laboratory Press, pp. 8.46-8.52 and pp. 11.2-11.19.*

Kappeler. Characterization of recombinant camel chymosin reveals superior properties for the coagulation of bovine and camel milk. Biochemical and Biophysical Research Communications 342 (2006) 647-654.*

LaVallie. Production of Recombinant Proteins in *Escherichia coli*. Current Protocols in Protein Science (1995) 5.1.1-5.1.8.*

Gilliland et al.; "The Three-Dimensional Structure of Recombinant Bovine Chymosin at 2.3 Å Resolution"; *Proteins: Structure, Function, and Genetics*; 8(1): 82-101 (Jan. 1990).

Jensen et al.; "Camel and bovine chymosin: the relationship between their structures and cheese-making properties"; *Acta Crystallographica*; 69(5): 901-913 (May 2013)(published online Apr. 2013).

Pitts et al.; "Expression and characterisation of chymosin pH optima mutants produced in *Trichoderma reesei*"; *Journal of Biotechnology*, 28(1): 69-83 (Mar. 1993).

Strop et al.; "Engineering Enzyme Subsite Specificity: Preparation, Kinetic Characterization, and X-ray Analysis at 2.0-Å Resolution of Val111Phe Site-Mutated Calf Chymosin"; *Biochemistry*, 29: 9863-9871 (Oct. 1990).

Chitpinityol, et al.; "Site-specific mutations of calf chymosin B which influence milk-clotting activity"; *Food Chemistry*, 62(2): 133-139 (Jun. 1998).

Suzuki et al.; "Alteration of catalytic properties of chymosin by site-directed mutagenesis"; *Protein Engineering*, 2(7): 563-569 (May 1989).

Suzuki et al.; "Site-directed mutagenesis reveals functional contribution of Thr218, Lys220 and Asp 304 in chymosin"; *Protein Engineering*, 4(1): 69-71 (Oct. 1990).

Van Den Brink et al.; "Increased production of chymosin by glycosylation"; *Journal of Biotechnology*, 125(2): 304-310 (Sep. 2006)(published online Apr. 2006).

Williams et al.; "Mutagenesis, biochemical characterization and X-ray structural analysis of point mutants of bovine chymosin"; *Protein Engineering*; 10(9): 991-997 (Sep. 1997).

Zhang et al.; "Functional implications of disulfide bond, Cys45-Cys50, in recombinant prochymosin"; *Biochimica et Biophysica Acta*, 1343(2): 278-286 (Dec. 1997).

PCT International Search Report issued in application PCT/EP2015/054020 dated Jul. 6, 2015.

Beppu,et al., "Modification of Milk-clotting aspartic proteases, chymosin and mucor rennin," *GBF Monographs*, pp. 87-92 (Dec. 1989).

Preprochymosin b, A9LY78,UniProt, May 16, 2012, [searched on Mar. 17, 2017]. URL: https://www.uniprot.org/A9LY78.txt?version=21.

Kageyama, "New World Monkey Pepsinogens A and C, and Prochymosins, Purification, Characterization of Enzymatic Properties, cDNA Cloning, and Molecular Evolution," *Journal of Biochemistry*, vol. 127, pp. 761-770 (Feb. 2000).

Database UniProt [Online] Oct. 1, 2000 (Oct. 1, 2000),"SubName: Full=Prochymosin {ECO:0000313|EMBL:AAF27315.1};", retrieved from EBI accession No. UniProt:Q9N1P5 Database accession No. Q9N1P5.

Database UniProt [Online] Feb. 5, 2008 (Feb. 5, 2008), "SubName: Full=Preprochymosin b {ECO:0000313|EMBL:ABX55935.1}; EC=3.4.23.4 {ECO:0000313|EMBL:ABX55935.1};", retrieved from EBI accession No. UniProt:A9LY78 Database accession No. A9LY78; -& Juan Andres Vallejo et al: "Cloning and Expression of Buffalo Active Chymosin in Pichia pastoris",Journal of Agricultural and Food Chemistry, vol. 56, No. 22, Nov. 26, 2008 (Nov. 26, 2008), pp. 10606-10610, XP055004003, ISSN: 0021-8561, DOI: 10.1021/jf802339e.

Database UniProt [Online] Nov. 1, 1990 (Nov. 1, 1990), "RecName: Full=Chymosin; EC=3.4.23.4; AltName: Full=Preprorennin; Flags: Precursor;", retrieved from EBI accession No. UniProt:P18276 Database accession No. P18276 ; -& J. Pungercar et al: "Complete primary structure of lamb preprochymosin deduced from cDNA", Nucleic Acids Research, vol. 18, No. 15, Aug. 11, 1990 (Aug. 11, 1990), pp. 4602-4602, XP055314297, GB ISSN: 0305-1048, DOI: 10.1093/nar/18.15.4602.

Database UniProt [Online] Mar. 20, 2007 (Mar. 20, 2007), "SubName: Full=Preprochymosin {ECO:0000313|EMBL:ABN13683.1};", retrieved from EBI accession No. UniProt:A3F4M4 Database accession No. A3F4M4.

Database Geneseq [Online] Jan. 2, 2014 (Jan. 2, 2014), "Bovine derived mature chymosin B variant H76Q.", retrieved from EBI accession No. GSP:BAY37837 Database accession No. BAY37837; -& WO 2013/164479 A2 (DSM IP Assets BV [NL]) Nov. 7, 2013 (Nov. 7, 2013).

Office Action issued in co-pending U.S. Appl. No. 14/402,567, dated Aug. 31, 2017 (US2015/0173383).

Vallejo, et al., "Cloning and Expression of Buffalo Active Chymosin in Pichia pastoris," *J. Agric. Food Chem.*, vol. 56, No. 22, pp. 10606-10610 (Nov. 2008).

Office Action issued in co-pending U.S. Appl. No. 14/402,567, dated Apr. 17, 2017 (US2015/0173383).

Houen, et al., "The Primary Structure and Enzymic Properties of Porcine Prochymosin and Chymosin," *Int. J. Biochem. Cell Biol.*, vol. 28, No. 6, pp. 667-675 (1996).

Restriction Requirement issued in co-pending U.S. Appl. No. 14/402,567, dated Dec. 27, 2016 (US2015/0173383).

U.S. Appl. No. 16/302,590, filed Nov. 16, 2018, Jaeckel, et al.

U.S. Appl. No. 61/642,095, filed May 3, 2012, Dekker et al.

Albert et al., "Protein Engineering Aspartic Proteinases: Site-Directed Mutagenesis, Biochemical Characterisation, and X-Ray Analysis of Chymosins with Substituted Single Amino Acid Substitutions and Loop Replacements," in Aspartic Proteinases, Chapter 23, pp. 169-178 (1998) (James, ed.).

Bansal et al., "Suitability of recombinant camel (*Camelus dromedarius*) chymosin as a coagulant for Cheddar cheese," International Dairy Journal 19 (2009) 510-517.

(56) References Cited

OTHER PUBLICATIONS

Claverie-Martin et al., "Aspartic Proteases Used in Cheese Making," in Industrial Enzymes pp. 207-219 (2007) (J. Polaina and A.P. MacCabe, eds.).

Chen et al., "Functional Implications of Disulfide Bond, Cys206-Cys210, in Recombinant Prochymosin (Chymosin)," Biochemistry 2000, 39, 12140-12148 (Published online Sep. 2000).

Kappeler et al. "Compositional and Structural Analysis of Camel Milk Proteins with Emphasis on Protective Proteins," ETH Zurich Research Collection, Dissertation, ETH No. 12947, pp. 1-137 (1998).

Moller et al., "Comparison of the Hydrolysis of Bovin κ-Casein by Camel and Bovine Chymosin: A Kinetic and Specificity Study," Journal of Agricultural and Food Chemistry, 60(21):5454-5460 (May 2012) (with NCBI extract).

Børsting et al., "Impact of selected coagulants and starters on primary proteolysis and amino acid release related to bitterness and structure of reduced-fat Cheddar cheese", Dairy Sci. & Technol. (Oct. 2012) vol. 92, pp. 593-612.

Creamer et al., "Rheological Evaluation of Maturing Cheddar Cheese", Journal of Food Science (1982) vol. 47, pp. 631-636.

Ehren et al., "Protein engineering of improved prolyl endopeptidases for celiac sprue therapy", Protein Engineering, Design & Selection (Oct. 2008) vol. 21, No. 12, pp. 699-707.

Filippovich et al. "Radicals," pp. 38-43 (2005).

Govindarajan et al., "Mapping of Amino Acid Substitutions Conferring Herbicide Resistance in Wheat Glutathione Transferase", ACS Synthetic Biology (Jun. 2014) vol. 4, pp. 221-227.

Gustchina et al., "Post X-ray crystallographic studies of chymosin: the existence of two structural forms and the regulation of activity by the interaction with the histidine-proline cluster of κ-casein", FEBS Letters (1996) vol. 379 pp. 60-62.

Kumar et al., "Chymosin and other milk coagulants: sources and biotechnological interventions", Critical Reviews in Biotechnology (2010) vol. 30 No. 4, pp. 243-258.

McSweeney "Biochemistry of cheese ripening", International Journal of Dairy Technology, (2004) vol. 57, No. 2/3, pp. 127-144.

Moynihan et al., "Effect of camel chymosin on the texture, functionality, and sensory properties of low-moisture, part-skim Mozzarella cheese", J. Dairy Sci. (2013) vol. 97, pp. 85-96.

Newman et al., "X-ray Analyses of Aspartic Proteinases IV Structure and Refinement at 2•2 Å Resolutions of Bovine Chymosin", J. Mol. Biol. (1991) vol. 221, pp. 1295-1309.

Palmer et al., "Bovine Chymosin: A Computational Study of Recognition and Binding of Bovine κ-Casein", Biochemistry (Feb. 2010) vol. 49, pp. 2563-2573.

Schechter et al., "On the Size of the Active Site in Proteases", Biochemical and Biophysical Research Communications (1967) vol. 27, No. 2 pp. 157-162.

Sørensen et al., "Hot-Spot Mapping of the Interactions between Chymosin and Bovine κ-Casein", Journal of Agricultural and Food Chemistry (Jul. 2013) vol. 61, pp. 7949-7959.

Struder et al., "Residue mutations and their impact on protein structure and function: detecting beneficial and pathogenic changes," Biochem. J. (2013) 449, 581-594.

Visser et al., "Peptide substrates for chymosin (rennin)" Biochem. J. (1987) vol. 244, pp. 553-558.

Møller, et al., "Camel and Bovine Chymosin Hydrolysis of Bovine αs1- and β-Caseins Studied by Comparative Peptide Mapping," Journ. of Agriculture and Food Chemistry, vol. 60, No. 45, pp. 11421-11432 (Oct. 2012).

V. V. Starovoitova et al. "Comparative Investigation of Functional Properties of Calf Chymosin and its Recombinant Forms," Biohimiya, 2006, tom 71, vyp. 3, s. 402-407 (in Russian).

Studer et al., "Residue mutations and their impact on protein structure and function: detecting beneficial and pathogenic changes," Biochem. J. (2013) 449, 581-594.

* cited by examiner

Figure 1

```
                         1                                                          50
Bos_bovis_chymosin_B    MRCLVVLLAV FALSQGAEIT RIPLYKGKSL RKALKEHGLL EDFLQKQQYG
               Sheep    MRCLVVLLAV FALSQGAEIT RIPLYKGKPL RKALKERGLL EDFLQKQQYG
        C._bactrianus   MRCLVVLLAA LALSQASGIT RIPLHKGKTL RKALKERGLL EDFLQRQQYA
   Camelus_dromedarius  MRCLVVLLAA LALSQASGIT RIPLHKGKTL RKALKERGLL EDFLQRQQYA
                 Pig    .IRGRVLLAV LALSQGSGIT RVPLRKGKSL RKELKERGLL EDFLQKQPYA
                 Rat    MRCFVLLLAV LAIAQSHVVT RIPLHKGKSL RNTLKEQGLL EDFLRRHQYE 51                                                         100
Bos_bovis_chymosin_B    ISSKYSGFGE VASVPLTNYL DSQYFGKIYL GTPPQEFTVL FDTGSSDFWV
               Sheep    VSSEYSGFGE VASVPLTNYL DSQYFGKIYL GTPPQEFTVL FDTGSSDFWV
        C._bactrianus   VSSKYSSLGK VAREPLTSYL DSQYFGKIYI GTPPQEFTVV FDTGSSDLWV
   Camelus_dromedarius  VSSKYSSLGK VAREPLTSYL DSQYFGKIYI GTPPQEFTVV FDTGSSDLWV
                 Pig    LSSKYSSFGE VASEPLTNYL DTQYFGKIYI GTPPQEFTVV FDTGSSELWV
                 Rat    FSEKNSNIGM VASEPLTNYL DSEYFGLIYV GTPPQEFKVV FDTGSSELWV 101                                                        150
Bos_bovis_chymosin_B    PSIYCKSNAC KNHQRFDPRK SSTFQNLGKP LSIHYGTGSM QGILGYDTVT
               Sheep    PSIYCKSNAC KNHQRFDPRK SSTFQNLGKP LSIRYGTGSM QGILGYDTVT
        C._bactrianus   PSIYCKSNAC KNHHRFDPRK SSTFRNLGKP LSIHYGTGSI EGFLGYDTVT
   Camelus_dromedarius  PSIYCKSNVC KNHHRFDPRK SSTFRNLGKP LSIHYGTGSM EGFLGYDTVT
                 Pig    PSVYCKSDAC QNHHRFNPSK SSTFQNLDKP LSIQYGTGSI QGFLGYDTVM
                 Rat    PSVYCSSKVC RNHNRFDPSK SFTFQNLSKP LFVQYGTGSV EGFLAYDTVT 151                                                        200
Bos_bovis_chymosin_B    VSNIVDIQQT VGLSTQEPGD VFTYAEFDGI LGMAYPSLAS EYSIPVFDNM
               Sheep    VSNIVDIQQT VGLSTQEPGD VFTYAEFDGI LGMAYPSLAS EYSVPVFDNM
        C._bactrianus   VSNIVDPNQT VGLSTEQPGE VFTYSEFDGI LGLAYPSLAS EYSVPVFDNM
   Camelus_dromedarius  VSNIVDPNQT VGLSTEQPGE VFTYSEFDGI LGLAYPSLAS EYSVPVFDNM
                 Pig    VAGIVDAHQT VGLSTQEPSD IFTYSEFDGI LGLGYPELAS EYTVPVFDNM
                 Rat    VSDIVVPHQT VGLSTEEPGD IFTYSPFDGI LGLAYPTFAS KYSVPIFDNM 201                                                        250
Bos_bovis_chymosin_B    MNRHLVAQDL FSVYMDRNGQ ESMLTLGAID PSYYTGSLHW VPVTVQQYWQ
               Sheep    MDRRLVAQDL FSVYMDRSGQ GSMLTLGAID PSYYTGSLHW VPVTLQKYWQ
        C._bactrianus   MDRHLVARDL FSVYMDRNGQ GSMLTLGATD PSYYTGSLHW VPVTVQQYWQ
   Camelus_dromedarius  MDRHLVARDL FSVYMDRNGQ GSMLTLGAID PSYYTGSLHW VPVTLQQYWQ
                 Pig    MHRHLVAQDL FAVYMSRNDE GSMLTLGAID PSYYTGSLHW VPVTMQLYWQ
                 Rat    MNRHLVAQDL FSVYMSRNDQ GSMLTLGAID QSYFIGSLHW VPVTVQGYWQ 251                                                        300
Bos_bovis_chymosin_B    FTVDSVTISG VVVACEGGCQ AILDTGTSKL VGPSSDILNI QQAIGATQNQ
               Sheep    FTVDSVTISG AVVACEGGCQ AILDTGTSKL VGPSSDILNI QQAIGATQNQ
        C._bactrianus   VTVDSVTING VAVACVGGCQ AILDTGTSVL FGPSSDILKI QMAIGATENR
   Camelus_dromedarius  FTVDSVTING VAVACVGGCQ AILDTGTSVL FGPSSDILKI QMAIGATENR
                 Pig    FTVDSVTING VVVACNGGCQ AILDTGTSML AGPSSDILNI QMAIGATESQ
                 Rat    FTVDRITIND EVVACQGGCP AVLDTGTALL TGPGRDILNI QHAIGAVQGQ 301                                                        350
Bos_bovis_chymosin_B    YGEFDIDCDN LSYMPTVVFE INGKMYPLTP SAYTSQDQGF CTSGFQSENH
               Sheep    YGEFDIDCDS LSSMPTVVFE INGKMYPLTP YAYTSQEEGF CTSGFQGENH
        C._bactrianus   YGEFDVNCGS LRSMPTVVFE INGRDFPLAP SAYTSKDQGF CTSGFQGDNN
   Camelus_dromedarius  YGEFDVNCGN LRSMPTVVFE INGRDYPLSP SAYTSKDQGF CTSGFQGDNN
                 Pig    YGEFDIDCGS LSSMPTVVFE ISGRMYPLPP SAYTNQDQGF CTSGFQGDSK
                 Rat    HDQFDIDCWR LNFMPTVVFE INGREFPLPP SAYTNQFQGS CSSGFR..HG 351                         381
Bos_bovis_chymosin_B    SQKWILGDVF IREYYSVFDR ANNLVGLAKA I
               Sheep    SHQWILGDVF IREYYSVFDR ANNLVGLAKA I
        C._bactrianus   SELWILGDVF IREYYSVFDR ANNRVGLAKA I
   Camelus_dromedarius  SELWILGDVF IREYYSVFDR ANNRVGLAKA I
                 Pig    SQHWILGVVF IQEYYSVFDR ANNRVGLAKA I
                 Rat    SQMWILGDVF IREFYSVFDR ANNRVGLAKA I
```

Positions 296 and 294 in
Bovine Chymosin

# VARIANTS OF CHYMOSIN WITH IMPROVED MILK-CLOTTING PROPERTIES

SEQUENCE LISTING

The instant application contains a Sequence Listing which has been submitted electronically in ASCII format and is hereby incorporated by reference in its entirety. Said ASCII copy, created on Aug. 18, 2017, is named 030427-0240_SL.txt and is 21,651 bytes in size.

FIELD OF THE INVENTION

The present invention relates to variants of chymosin with improved milk-clotting properties.

BACKGROUND ART

Enzymatic coagulation of milk by milk-clotting enzymes, such as chymosin and pepsin, is one of the most important processes in the manufacture of cheeses. Enzymatic milk coagulation is a two-phase process: a first phase where a proteolytic enzyme, chymosin or pepsin, attacks K-casein, resulting in a metastable state of the casein micelle structure and a second phase, where the milk subsequently coagulates and forms a coagulum.

Chymosin (EC 3.4.23.4) and pepsin (EC 3.4.23.1), the milk clotting enzymes of the mammalian stomach, are aspartic proteases belonging to a broad class of peptidases.

When produced in the gastric mucosal cells, chymosin and pepsin occur as enzymatically inactive pre-prochymosin and pre-pepsinogen, respectively. When chymosin is excreted, an N-terminal peptide fragment, the pre-fragment (signal peptide) is cleaved off to give prochymosin including a pro-fragment. Prochymosin is a substantially inactive form of the enzyme which, however, becomes activated under acidic conditions to the active chymosin by autocatalytic removal of the pro-fragment. This activation occurs in vivo in the gastric lumen under appropriate pH conditions or in vitro under acidic conditions.

The structural and functional characteristics of bovine, i.e. Bos taurus, pre-prochymosin, prochymosin and chymosin have been studied extensively. The pre-part of the bovine pre-prochymosin molecule comprises 16 aa residues and the pro-part of the corresponding prochymosin has a length of 42 aa residues. The active bovine chymosin comprises 323 aa is a mixture of two forms, A and B, both of which are active.

Chymosin is produced naturally in mammalian species such as bovines, camels, caprines, buffaloes, sheep, pigs, humans, monkeys and rats.

Bovine chymosin has for a number of years been commercially available to the dairy industry.

WO02/36752A2 (Chr. Hansen) describes recombinant production of camel chymosin.

WO2013/174840A1 (Chr. Hansen) describes mutants/variants of bovine and camel chymosin.

WO2013/164479A2 (DSM) describes mutants of bovine chymosin.

The references listed immediately below may in the present context be seen as references describing mutants of chymosin:

Suzuki et al: Site directed mutagenesis reveals functional contribution of Thr218, Lys220 and Asp304 in chymosin, Protein Engineering, vol. 4, January 1990, pages 69-71;

Suzuki et al: Alteration of catalytic properties of chymosin by site-directed mutagenesis, Protein Engineering, vol. 2, May 1989, pages 563-569;

van den Brink et al: Increased production of chymosin by glycosylation, Journal of biotechnology, vol. 125, September 2006, pages 304-310;

Pitts et al: Expression and characterisation of chymosin pH optima mutants produced in Tricoderma reesei, Journal of biotechnology, vol. 28, March 1993, pages 69-83;

M. G. Williams et al: Mutagenesis, biochemical characterization and X-ray structural analysis of point mutants of bovine chymosin, Protein engineering design and selection, vol. 10, September 1997, pages 991-997;

Strop et al: Engineering enzyme subsite specificity: preparation, kinetic characterization, and x-ray analysis at 2.0 ANG resolution of Val111phe site mutated calf chymosin, Biochemistry, vol. 29, October 1990, pages 9863-9871;

Supannee et al: Site-specific mutations of calf chymosin B which influence milk-clotting activity, Food Chemistry, vol. 62, June 1998, pages 133-139;

Zhang et al: Functional implications of disulfide bond, Cys45-Cys50, in recombinant prochymosin, Biochimica et biophysica acta, vol. 1343, December 1997, pages 278-286.

None of the prior art references mentioned above describe directly and unambiguously any of the chymosin mutants/variants as described/claimed below herein.

SUMMARY OF THE INVENTION

The problem to be solved by the present invention is to provide variants of chymosin with improved milk-clotting properties.

As discussed in working examples herein—the present inventors have identified a number of improved camel (see Example 6 herein) and bovine/camel (see Example 7 herein) chymosin variants.

Based on a comparative analysis of the camel and bovine variants—the present inventors identified a number of further amino acid positions that are herein important in the sense that by making a variant in one or more of these positions one may get an improved chymosin variant.

As known in the art—different natural wildtype chymosin polypeptide sequences obtained from different mammalian species (such as e.g. bovines, camels, sheep, pigs, or rats) are having a relatively high sequence similarity/identity.

In FIG. 1 herein this is exemplified by an alignment of herein relevant different chymosin sequences.

In view of this relatively close sequence relationship—it is believed that the 3D structures of different natural wildtype chymosins are also relatively similar.

In the present context—a natural obtained wildtype chymosin (such as bovine chymosin or camel chymosin) may herein be an example of a parent polypeptide—i.e. a parent polypeptide to which an alteration is made to produce a variant chymosin polypeptide of the present invention.

Without being limited to theory—it is believed that the herein discussed chymosin related amino acid positions are of general importance in any herein relevant chymosin enzyme of interest (e.g. chymosins of e.g. bovines, camels, sheep, pigs, rats etc)—in the sense that by making a variant in one or more of these positions one may get an improved chymosin variant in general (e.g. an improved bovine, camel, sheep, pig or rat chymosin variant).

As discussed herein—as a reference sequence for determining the amino acid position of a parent chymosin polypeptide of interest (e.g. camel, sheep, bovine etc) is herein used the public known bovine chymosin B preprochymosin sequence (Genbank accession number P00794—disclosed as SEQ ID NO: 1 herein).

The bovine chymosin B preprochymosin of SEQ ID NO: 1 may herein alternatively be termed Bovine (*Bos bovis*) chymosin B or simply bovine chymosin. The sequence is also shown in FIG. 1 herein.

Another herein relevant chymosin sequence is publically known *Camelius dromedarius* chymosin sequence of SEQ ID NO: 2 herein. It may herein alternatively be termed camel chymosin. The sequence is also shown in FIG. 1 herein.

In the present context it is believed that a parent chymosin polypeptide (e.g. from sheep or rat) that has at least 65% sequence identity with the mature polypeptide of SEQ ID NO: 1 (bovine chymosin) may herein be seen as sufficient structural related to e.g. bovine or camel chymosin in order to be improved by making a variant in any of the amino acid positions as described herein.

Accordingly, a first aspect of the invention relates to a method for making an isolated chymosin polypeptide variant comprising the steps:

(a): making an alteration at one or more positions in a parent polypeptide having chymosin activity, wherein the alteration is comprising a substitution, a deletion or an insertion in at least one amino acid position corresponding to any of positions 70; 75; 77; 79; 90; 102; 103; 108; 114; 117; 120; 124; 134; 154; 156; 163; 212; 222; 223; 224; 238; 246; 256; 261; K279V; L280; F281; R300D,E,S,T,N,Q,C,U,G,P,A,V,I,L,M,F,Y,W; G309; R312D,E,S,T,N,Q,C,U,G,P,A,V,I,L,M,F,Y,W; 320; 324; D325Q; 326; 331; 336; 346; 361; 367 and 379; and (b): producing and isolating the altered polypeptide of step (a) and thereby obtaining the isolated chymosin polypeptide variant, wherein the variant has chymosin activity;
and wherein:
(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and
(ii): the parent polypeptide has at least 65% sequence identity with the mature polypeptide of SEQ ID NO: 1 (bovine chymosin), which is from amino acid position 59 to amino acid position 381 of SEQ ID NO: 1;
and with the proviso that the isolated chymosin polypeptide variant is NOT a specific variant selected from the group consisting of:
Q246E+G309D+S329P+D337E;
R125Q+G128N+H204R+Q246E+S284T;
Y185F+R213Q+Q246E;
V261A+V263I+G309W+L311I+Y326F;
G128D+L188I+Y326F;
G128N+R312S+S313Y+Y326F;
G128N+R312S+S313Y+Y326F;
D117N+V261A+R312S;
D216S+L224V+V263I+F281V+G309D;
Y79S+L224V+L311I; and
R119S+L224V+T297S.

The proviso above may be seen as relating to above discussed WO2013/174840A1 (Chr. Hansen)—since in this document are explicitly described these specific variants.

As understood by the skilled person in the present context—the proviso only relates to the specific mentioned variants.

For instance, a variant only comprising the Q246E substitution (i.e. not G309D, S329P and/or D337E) is not such a specific variant within the proviso—i.e. it is not disclaimed in the present context.

As known in the art—the skilled person may, based on his common general knowledge, routinely produce and purify chymosin and chymosin variants.

Said in other words, once the skilled person is in possession of a herein relevant parent polypeptide having chymosin activity of interest (e.g. from bovines, camels, sheep, pigs, or rats) it is routine work for the skilled person to make a variant of such a parent chymosin of interest.

A second aspect of the invention relates to an isolated chymosin polypeptide variant obtained by the method of first aspect or any herein relevant embodiments thereof.

The term "obtained" in relation to the second aspect above should be understood as that the isolated chymosin polypeptide variant has been obtained by the method of first aspect or any herein relevant embodiments thereof.

Accordingly, the term "obtained" in relation to the second aspect should not be understood as obtainable.

As discussed herein—in working examples herein were made variants using the polypeptide of SEQ ID NO: 1 (Bovine) as parent polypeptide—such variant may herein be termed bovine chymosin variants.

Accordingly, a third aspect of the invention relates to an isolated chymosin polypeptide variant comprising:

(a): an alteration at one or more positions in a parent polypeptide having chymosin activity, wherein the alteration is comprising a substitution, a deletion or an insertion in at least one amino acid position corresponding to any of positions 70; 75; 77; 79; 90; 102; 103; 108; 114; 117; 120; 124; 134; 154; 156; 163; 212; 222; 223; 224; 238; 246; 256; 261; K279V; L280; F281; R300D,E,S,T,N,Q,C,U,G,P,A,V,I,L,M,F,Y,W; G309; R312D,E,S,T,N,Q,C,U,G,P,A,V,I,L,M,F,Y,W; 320; 324; D325Q; 326; 331; 336; 346; 361; 367 and 379; and (b): wherein the variant has chymosin activity;
and wherein:
(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and
(ii): the parent polypeptide has at least 90% sequence identity with the mature polypeptide of SEQ ID NO: 1 (bovine chymosin), which is from amino acid position 59 to amino acid position 381 of SEQ ID NO: 1; and
(iii): the isolated variant polypeptide has less than 100% sequence identity with the mature polypeptide of SEQ ID NO: 1 (bovine chymosin);
and with the proviso that the isolated chymosin polypeptide variant is NOT a specific variant selected from the group consisting of:
Q246E+G309D+S329P+D337E;
R125Q+G128N+H204R+Q246E+S284T;
Y185F+R213Q+Q246E;
V261A+V263I+G309W+L311I+Y326F;
G128D+L188I+Y326F;
G128N+R312S+S313Y+Y326F;
G128N+R312S+S313Y+Y326F; and
D117N+V261A+R312S;
D216S+L224V+V263I+F281V+G309D
Y79S+L224V+L311I and
R119S+L224V+T297S.

As discussed herein—in working examples herein were made variants using the polypeptide of SEQ ID NO: 2 (camel chymosin) as parent polypeptide—such variant may herein be termed camel chymosin variant.

Accordingly, a fourth aspect of the invention relates to an isolated chymosin polypeptide variant comprising:

(a): an alteration at one or more positions in a parent polypeptide having chymosin activity, wherein the alteration is comprising a substitution, a deletion or an insertion in at least one amino acid position corresponding to any of positions 70; 75; 77; 79; 90; 102; 103; 108; 114; 117; 120; 124; 134; 154; 156; 163; 212; 222; 223; 224; 238; 246; 256; 261; K279V; L280; F281; R300D,E,S,T,N,Q,C,U,G,P,A,V, I,L,M,F,Y,W; G309; R312D,E,S,T,N,Q,C,U,G,P,A,V,I,L,M, F,Y,W; 320; 324; D325Q; 326; 331; 336; 346; 361; 367 and 379; and (b): wherein the variant has chymosin activity;
and wherein:

(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and (ii): the parent polypeptide has at least 90% sequence identity with the mature polypeptide of SEQ ID NO: 2 (Camel chymosin), which is from amino acid position 59 to amino acid position 381 of SEQ ID NO: 2; and (iii): the isolated variant polypeptide has less than 100% sequence identity with the mature polypeptide of SEQ ID NO: 2 (camel chymosin);

and with the proviso that the isolated chymosin polypeptide variant is NOT a specific variant selected from the group consisting of:

Q246E+G309D+S329P+D337E;
R125Q+G128N+H204R+Q246E+S284T;
Y185F+R213Q+Q246E;
V261A+V263I+G309W+L311I+Y326F;
G128D+L188I+Y326F;
G128N+R312S+S313Y+Y326F;
G128N+R312S+S313Y+Y326F;
D117N+V261A+R312S;
D216S+L224V+V263I+F281V+G309D;
Y79S+L224V+L311I; and
R119S+L224V+T297S.

An isolated chymosin polypeptide variant as described herein may be used according to the art—e.g. to make a food or feed product of interest (such as e.g. a milk based product of interest that e.g. could be a cheese product).

Accordingly, a fifth aspect of the invention relates to a method for making a food or feed product comprising adding an effective amount of the isolated chymosin polypeptide variant as described herein to the food or feed ingredient(s) and carrying our further manufacturing steps to obtain the food or feed product.

Embodiment of the present invention is described below, by way of examples only.

Definitions

All definitions of herein relevant terms are in accordance of what would be understood by the skilled person in relation to the herein relevant technical context.

The term "chymosin" relates to an enzyme of the EC 3.4.23.4 class. Chymosin has a high specificity and it clots milk by cleavage of a single 105-Ser-Phe-|-Met-Ala-108 bond in kappa-chain of casein. An alternative name used in the art is rennin.

The term "chymosin activity" relates to chymosin activity of a chymosin enzyme as understood by the skilled person in the present context.

The skilled person knows how to determine herein relevant chymosin activity.

In working Example 4 herein is provided an example of a standard method to determine specific chymosin activity—alternatively termed clotting activity or milk clotting activity.

In working Example 5 herein is provided an example of a standard method to determine proteolytical activity.

As known in the art—the herein relevant so-called C/P ratio is determined by dividing the specific clotting activity (C) with the proteolytical activity (P).

As known in the art—a higher C/P ratio implies generally that the loss of protein during e.g. cheese manufacturing due to non-specific protein degradation is reduced, i.e. the yield of cheese is improved, and that the development of bitter taste in the cheese during maturation is reduced.

The term "isolated variant" means a variant that is modified by the hand of man. In one aspect, the variant is at least 1% pure, e.g., at least 5% pure, at least 10% pure, at least 20% pure, at least 40% pure, at least 60% pure, at least 80% pure, and at least 90% pure, as determined by SDS PAGE.

The term "mature polypeptide" means a peptide in its final form following translation and any post-translational modifications, such as N terminal processing, C terminal truncation, glycosylation, phosphorylation, etc. In the present context may a herein relevant mature chymosin polypeptide be seen as the active chymosin polypeptide sequence—i.e. without the pre-part and/or pro-part sequences. Herein relevant examples of a mature polypeptide are e.g. the mature polypeptide of SEQ ID NO: 1 (bovine chymosin), which is from amino acid position 59 to amino acid position 381 of SEQ ID NO: 1 or the mature polypeptide of SEQ ID NO: 2 (camel chymosin), which is from amino acid position 59 to amino acid position 381 of SEQ ID NO: 2.

The term "parent" or "parent polypeptide having chymosin activity" means a polypeptide to which an alteration is made to produce the enzyme variants of the present invention. The parent may be a naturally occurring (wild-type) polypeptide or a variant thereof.

The term "Sequence Identity" relates to the relatedness between two amino acid sequences or between two nucleotide sequences.

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later.

The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment).

The term "variant" means a peptide having chymosin activity comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

The amino acid may be natural or unnatural amino acids—for instance, substitution with e.g. a particularly D-isomers (or D-forms) of e.g. D-alanine could theoretically be possible.

The term "wild-type" chymosin peptide means a chymosin expressed by a naturally occurring organism, such as a mammalian (e.g. camel or bovine) found in nature.

DRAWINGS

FIG. 1: An alignment of herein relevant different chymosin sequences. The shown "Bos_bovis_chymosin_B" is bovine chymosin of SEQ ID NO: 1 herein and the shown "Camelus_dromedarius" is camel chymosin of SEQ ID NO: 2 herein. Using bovine chymosin of SEQ ID NO: 1 as reference sequence as described herein is can e.g. be seen that bovine chymosin has "V" in position 10 and camel chymosin has "A" in the same position 10. It may e.g. also be seen that bovine/Rat have "Q" in position 352 and Camel/C._bactrianus have "E" in the same position 352. FIG. 1 discloses SEQ ID NOS 1, 3, 4, 2, 5 and 6, respectively, in order of appearance.

In relation to the chymosin sequences shown in FIG. 1—sheep has 94.5% sequence identity with bovine SEQ ID NO: 1; C._bactrianus has 83.2% sequence identity with bovine SEQ ID NO: 1; Camelus_dromedarius (camel chymosin of SEQ ID NO: 2) has 84% sequence identity with bovine SEQ ID NO: 1; pig has 80.3% sequence identity with bovine SEQ ID NO: 1 and rat has 71.9% sequence with bovine identity SEQ ID NO: 1.

As understood by the skilled person in the present context—herein relevant sequence identity percentages of mature polypeptide sequences of e.g. sheep, C._bactrianus, camel, pig or rat chymosin with the mature polypeptide of SEQ ID NO: 1 (bovine chymosin—i.e. amino acid positions 59 to 381 of SEQ ID NO: 1) are relatively similar to above mentioned sequence identity percentages.

FIG. 2: The 3D structure of bovine chymosin—the 3D structure is public available. As an example are shown where the amino acid positions 296 and 294 are present in bovine Chymosin.

Figure 3:
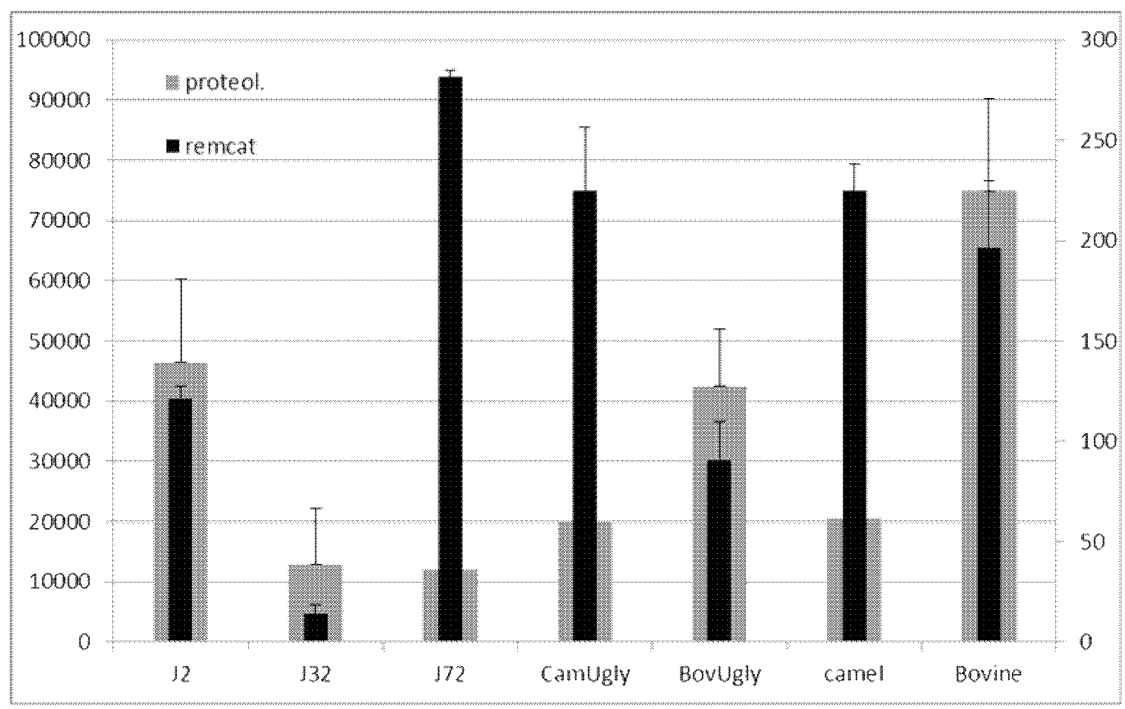

FIG. 3: Show a graphical representation the REMCAT and Proteol values of a number of chymosin variants.

Figure 4:
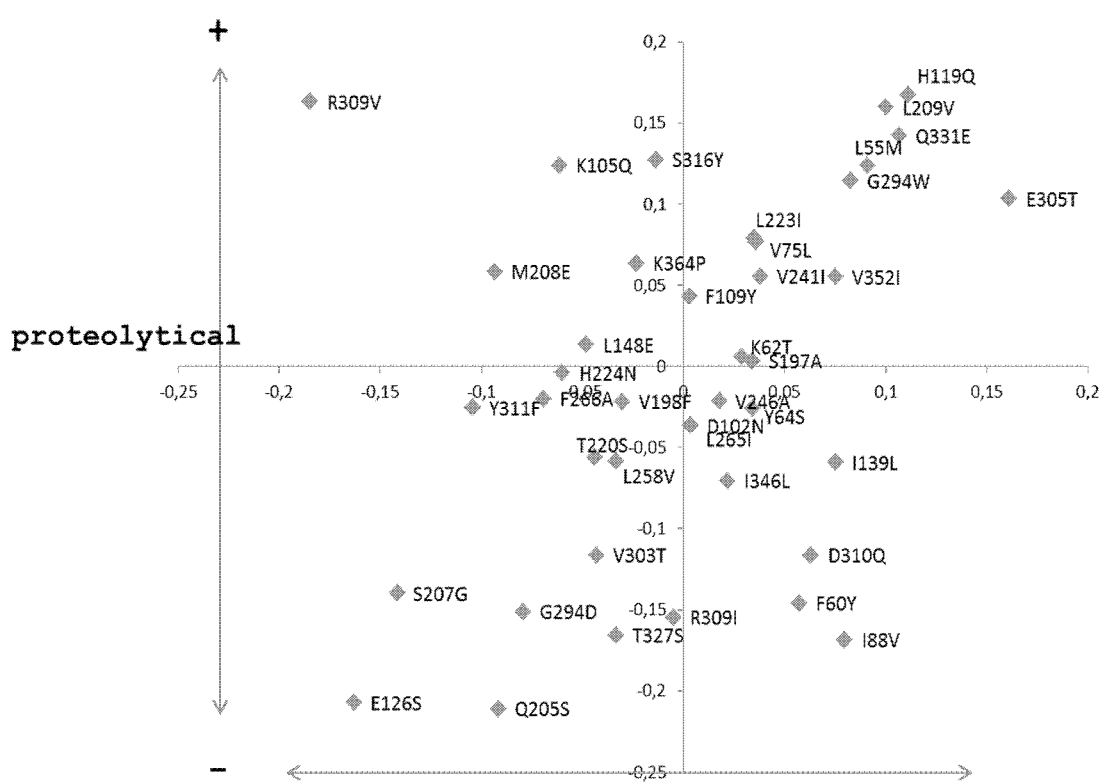

FIG. 4: PCA plot of effect of individual substitutions. All position numbers are 15 lower than numbers used in text.

DETAILED DESCRIPTION OF THE INVENTION

Determining the Amino Acid Position of a Chymosin of Interest

As discussed above—as a reference sequence for determining the amino acid position of a herein relevant chymosin polypeptide of interest (e.g. camel, sheep, bovine etc.) is herein used the public known bovine chymosin sequence disclosed as SEQ ID NO: 1 herein.

For purposes of the present invention, the polypeptide disclosed in SEQ ID NO: 1 (bovine chymosin) is used to determine the corresponding amino acid residue in another chymosin polypeptide. The amino acid sequence of another chymosin polypeptide is aligned with the polypeptide disclosed in SEQ ID NO: 1, and based on the alignment, the amino acid position number corresponding to any amino acid residue in the polypeptide disclosed in SEQ ID NO: 1 is determined using the ClustalW algorithm as described in working Example 1 herein.

Identification of the corresponding amino acid residue in another chymosin polypeptide can be confirmed by using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later.

Based on above well known computer programs—it is routine work for the skilled person to determine the amino acid position of a herein relevant chymosin polypeptide of interest (e.g. camel, sheep, bovine etc.).

In FIG. 1 herein is shown an example of an alignment.

Just as an example—in FIG. 1 can e.g. be seen that herein used bovine reference SEQ ID NO: 1 has a "G" in position 50 and "Camelus_dromedarius" (SEQ ID NO: 2 herein) has an "A" in this position 50.

Nomenclature of Variants

In describing the variants of the present invention, the nomenclature described below is adapted for ease of reference. The accepted IUPAC single letter or three letter amino acid abbreviations are employed.

The specific variants discussed in this "nomenclature" section below may not be herein relevant variants of the present invention—i.e. this "nomenclature" section is just to describe the herein relevant used nomenclature as such.

Substitutions.

For an amino acid substitution, the following nomenclature is used: Original amino acid, position, substituted amino acid. Accordingly, a theoretical substitution of threonine with alanine at position 226 is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. A substitution e.g. designated "226A" refers to a substitution of a parent amino acid (e.g. T, Q, S or another parent amino acid) with alanine at position 226.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G-K-A    |

Multiple Alterations.

Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different Substitutions.

Where different substitutions can be introduced at a position, the different substitutions are separated by a comma, e.g., "Arg170Tyr,Glu" or "R170Y,E" represents a substitution of arginine with tyrosine or glutamic acid at position 170. Thus, "Tyr167Gly,Ala+Arg170Gly,Ala" or "Y167G,A+R170G,A" designates the following variants: "Tyr167Gly+Arg170Gly", "Tyr167Gly+Arg170Ala", "Tyr167Ala+Arg170Gly", and "Tyr167Ala+Arg170Ala".

A Method for Making an Isolated Chymosin Polypeptide Variant

As discussed above—as known in the art, the skilled person may, based on his common general knowledge, routinely produce and purify chymosin and chymosin variants.

Said in other words, once the skilled person is in possession of a herein relevant parent polypeptide having chymosin activity of interest (e.g. from bovines, camels, sheep, pigs, or rats) it is routine work for the skilled person to make a variant of such a parent chymosin of interest.

An example of a suitable method to produce and isolate a chymosin (variant or parent) may be by well known e.g. fungal recombinant expression/production based technology as e.g. described in WO02/36752A2 (Chr. Hansen).

It is also routine work for the skilled person to make alteration at one or more positions in a parent polypeptide having chymosin activity, wherein the alteration is comprising a substitution, a deletion or an insertion in at least one amino acid position.

As known to the skilled person—this may e.g. be done by so-called site directed mutagenesis and recombinant expression/production based technology.

It is also routine work for the skilled person to determine if a herein relevant parent polypeptide (e.g. camel or bovine wildtype chymosin) and/or a herein relevant variant has chymosin activity or not.

As known in the art—chymosin activity may be determined by the so-called C/P ratio, which is determined by dividing the specific clotting activity (C) with the proteolytical activity (P).

As known in the art—a higher C/P ratio implies generally that the loss of protein during e.g. cheese manufacturing due to non-specific protein degradation is reduced, i.e. the yield of cheese is improved, and that the development of bitter taste in the cheese during maturation is reduced.

In working example 4 herein is described a suitable method to determine the specific clotting activity (C) and in working example 5 herein is described a suitable method to determine proteolytical activity (P).

Preferably, an isolated chymosin polypeptide variant as described herein is a variant, wherein the variant has a chymosin activity giving a higher C/P ratio as compared to the C/P ratio of bovine chymosin comprising the mature polypeptide of SEQ ID NO: 1 herein.

Preferably, an isolated chymosin polypeptide variant as described herein is a variant, wherein the variant has a chymosin activity giving a higher C/P ratio as compared to the C/P ratio of camel chymosin comprising the mature polypeptide of SEQ ID NO: 2 herein.

More preferably, an isolated chymosin polypeptide variant as described herein is a variant, wherein the variant has
   a chymosin activity giving a higher C/P ratio as compared to the C/P ratio of bovine chymosin comprising the mature polypeptide of SEQ ID NO: 1 herein; and
   a chymosin activity giving a higher C/P ratio as compared to the C/P ratio of camel chymosin comprising the mature polypeptide of SEQ ID NO: 2 herein.

As discussed above—as a reference sequence for determining the amino acid position of a herein relevant chymosin polypeptide of interest (e.g. camel, sheep, bovine etc) is herein used the public known bovine chymosin sequence disclosed as SEQ ID NO: 1 herein.

As discussed above—based on e.g. the computer sequence alignment programs discussed herein—it is routine work for the skilled person to determine the herein relevant amino acid position of a herein relevant chymosin polypeptide of interest (e.g. camel, sheep, bovine etc).

The term "the parent polypeptide has at least 65% sequence identity with the mature polypeptide of SEQ ID NO: 1 (bovine chymosin)" of e.g. the method of the first aspect herein may be seen as relating to a sequence based limitation of the parent chymosin polypeptide used to make a herein relevant variant thereof.

Said in other words—a mature parent chymosin polypeptide (e.g. sheep or pig) that has at least 65% sequence identity with the mature Bovine chymosin is believed to be sufficient structural identical to e.g. Bovine or Camel chymosin in order to be herein relevant—i.e. in the present context it is believed that a mature parent chymosin polypeptide (e.g. from e.g. sheep or rat) that has at least 65% sequence identity with the mature polypeptide of SEQ ID NO: 1 (bovine chymosin) may herein be seen as sufficient structural related to e.g. bovine or camel chymosin in order to be improved by making a variant in any of the amino acid positions as described herein.

The camel chymosin polypeptide of SEQ ID NO: 2 has 84% sequence identity with the bovine polypeptide of SEQ ID NO: 1 (i.e. the complete SEQ ID NO: 1 from position 1 to 381, which includes pre and pro sequence).

As understood by the skilled person in the present context—a herein relevant parent polypeptide having chymosin activity may already e.g. be a variant of e.g. a corresponding wildtype chymosin.

For instance, a camel chymosin variant with e.g. 5-10 alterations (e.g. substitutions) as compared to wildtype camel chymosin polypeptide of SEQ ID NO: 2 will still be a parent polypeptide that has at least 65% sequence identity with the mature polypeptide of SEQ ID NO: 1 (Bovine) as required in e.g. first aspect herein.

Said in other words, a herein relevant isolated chymosin polypeptide variant may comprise alterations (e.g. substitutions) in other position than the positions of e.g. the first aspect herein.

In relation to the chymosin sequences shown in FIG. 1 herein—sheep has 94.5% sequence identity with bovine SEQ ID NO: 1; C._bactrianus has 83.2% sequence identity with bovine SEQ ID NO: 1; pig has 80.3% sequence identity with bovine SEQ ID NO: 1 and rat has 71.9% sequence with bovine identity SEQ ID NO: 1.

As understood by the skilled person in the present context—herein relevant sequence identity percentages of e.g. mature sheep, C._bactrianus, camel, pig or rat chymosin with the mature polypeptide of SEQ ID NO: 1 (bovine chymosin—i.e. amino acid positions 59 to 381 of SEQ ID NO: 1) are relatively similar to above mentioned sequence identity percentages.

Preferred Variants:

As discussed above—e.g. the first aspect relates to an isolated chymosin polypeptide variant, wherein the alteration is comprising a substitution, a deletion or an insertion in at least one amino acid position corresponding to any of positions 70; 75; 77; 79; 90; 102; 103; 108; 114; 117; 120; 124; 134; 154; 156; 163; 212; 223; 224; 238; 246; 256; 261; K279V; L280; F281; R300D,E,S,T,N,Q,C,U,G,P,A,V,I,L,M,F,Y,W; G309; R312D,E,S,T,N,Q,C,U,G,P,A,V,I,L,M,F,Y,W; 320; 324; D325Q; 326; 331; 336; 346; 361; 367 and 379.

A preferred embodiment relates to an isolated chymosin polypeptide variant, wherein the alteration comprises a substitution, a deletion or an insertion in at least one amino acid position corresponding to any of positions of e.g. the first aspect herein.

It may be preferred that at least one alteration is a substitution—i.e. a herein relevant preferred embodiment relates to an isolated chymosin polypeptide variant, wherein the alteration is comprising a substitution in at least one amino acid position corresponding to any of positions e.g. the first aspect herein.

Preferably, an isolated chymosin polypeptide variant, wherein the alteration is comprising a substitution in at least one amino acid position corresponding to any of positions L70M; F75Y; K77T; Y79S; V90L; D102N; I103V; K120Q; F124Y; H134Q; I154L; D156V; L163E; S212A; S222G; M223E; L224V; L238I; Q246E; V256I; V261A; K279V; L280I; F281A; R300D,E,S,T,N,Q; R312D,E,S,T,N,Q; E320T; R324V; D325Q; Y326F; K336D,E,S,T,N,Q,C,U,G, P,A,V,I,L,M,F,Y,W; S331Y; Q346E; I361L; V367I; or K379P.

Preferably, the substitution is wherein the substitution is Q246E; K279V; R300Q; R312S; Y326F or K336D,E,S,T, N,Q, wherein a preferred K336 substitution is K336Q.

As understood by the skilled person in the present context—if the parent chymosin polypeptide already has e.g. "V" in position 156 then is does not make sense to talk about making the substitution 156V for this specific parent chymosin polypeptide. As can be seen in FIG. 1 herein—rat wildtype chymosin has "V" in position 156—the substitution 156V may be seen as herein irrelevant for the specific rat chymosin polypeptide sequence of FIG. 1.

As understood by the skilled person in the present context—if the parent chymosin polypeptide does not have e.g. "D" in position 156 then is does not make sense to talk about making the substitution D156V for this specific parent chymosin polypeptide. As can be seen in FIG. 1 herein—rat wildtype chymosin has "V" in position 156—the substitution D156V may therefore be seen as herein irrelevant for the specific rat chymosin polypeptide sequence of FIG. 1.

In a preferred embodiment, the substitution is wherein the substitution is:
H134Q+Q246E+Y326F;
D117N+L280I+G309D;
H134Q+D156V+G309D;
D156V+Q246E+L280I;
D117N+H134Q+L280I;
D156V+G309D+Y326F;
D117N+D156V+D325M;
L280I+D325M+Y326F;
D117N+Q246E+Y326F;
D117N+H134Q+D325M;
N310Q+N349Q+K279V;
R300Q+N307D;
N307D+G309D;
N307D+R312S;
R300Q+K336Q;
N307D+K336Q;
G309D+R312S;
R300Q+N307D+G309D+R312S+K336Q;
N158Q+N349Q+R300Q+N307D+G309D+R312S+K336Q;
L280I+G309D+S331Y+T342S+D325Q;
L280I+G309D+L224V+E320T+T235S;
L280I+G309W+K77T+R324I;
L280I+G309D+H134Q+V213F+F281A;
L280I+G309D+V213F+E320T+V90L;
L280I+G309D+Q220S+L224V+H134Q;
L280I+G309W+L238I+T342S;
L280I+G309W+F75Y+Y79S;
L280I+G309D+F75Y+S331Y+Q346E;
L280I+G309D+L224V+I103V+L238I;
L280I+G309D+F124Y+Q346E+I154L;
L280I+G309D+I154L+V261A+V367I;
L280I+G309D+Y79S+L224V+S212A;
L280I+G309D+L70M+T342S;
L280I+G309D+H134Q+M223E+L70M;
L280I+G309D+Y79S+T342S+I154L;
L280I+G309D+Y79S+I103V+F281A;
L280I+G309D+V256I+V261A+K379P;
L280I+G309D+Q346E+K77T+T235S;
L280I+G309D+H239N+R324I+D325Q;
L280I+G309D+H134Q+V213F+F281A;
L280I+G309D+Y326F+L70M+D325Q;
L280I+G309D+H134Q+M223E+L70M;
L280I+G309W+S212A+V261A;
L280I+G309D+S331Y+L224V+Y326F;
L280I+G309D+K120Q+M223E+H239N;
L280I+G309D+H239N+R324I+D325Q;
L280I+G309W+L238I+T342S;
L280I+G309D+V213F+E320T+V90L;
L280I+G309D+L70M+T342S;
L280I+G309D+H134Q+V213F+F281A;
L280I+G309D+Y79S+L224V+S212A;
L280I+G309D+S331Y+L224V+Y326F;
L280I+G309D+H134Q+M223E+L70M;
L280I+G309W+L238I+T342S;
L280I+G309D+V213F+E320T+V90L; or
L280I+G309W+S212A+V261A.

In a more preferred embodiment, the substitution is wherein the substitution is:
D117N+L280I+G309D;
L280I+D325M+Y326F;
D117N+Q246E+Y326F;
R300Q+N307D+G309D+R312S+K336Q; or
N158Q+N349Q+R300Q+N307D+G309D+R312S+K336Q.

Preferred Parent Polypeptide Having Chymosin Activity:

Preferably, the parent polypeptide has at least 70% sequence identity with the mature polypeptide of SEQ ID NO: 1 (bovine chymosin), more preferably the parent polypeptide has at least 75% sequence identity with the mature polypeptide of SEQ ID NO: 1 (bovine chymosin).

Just as an example—a herein suitable relevant parent polypeptide could e.g. be bovine chymosin A—as known in the art bovine chymosin A may only have one amino acid difference as compared to bovine chymosin B of SEQ ID NO: 1 herein.

As discussed above—in working examples herein were made variants using the polypeptide of SEQ ID NO: 1 (Bovine) as parent polypeptide—such variant may herein be termed bovine chymosin variants.

Accordingly, in a preferred embodiment—the parent polypeptide has at least 90% sequence identity with the mature polypeptide of SEQ ID NO: 1 (bovine chymosin), more preferably the parent polypeptide has at least 95% sequence identity with the mature polypeptide of SEQ ID NO: 1 (bovine chymosin) and even more preferably the parent polypeptide has at least 97% sequence identity with the mature polypeptide of SEQ ID NO: 1 (bovine chymosin). It may be preferred that the parent polypeptide is the mature polypeptide of SEQ ID NO: 1 (bovine chymosin).

As understood by the skilled person in the present context—a herein relevant parent polypeptide having chymosin activity may already e.g. be a variant of e.g. a corresponding wildtype chymosin.

For instance, a bovine chymosin variant with e.g. 5-10 alterations (e.g. substitutions) as compared to mature wildtype bovine chymosin polypeptide of SEQ ID NO: 1 will still be a parent polypeptide that has at least 95% sequence identity with the mature polypeptide of SEQ ID NO: 1 (Bovine chymosin).

The mature polypeptide of SEQ ID NO: 1 (Bovine) is 323 amino acids long—accordingly, a bovine chymosin variant with e.g. 25 amino acid substitutions as compared to mature wildtype bovine chymosin polypeptide of SEQ ID NO: 1 will not be a parent polypeptide that has at least 95% sequence identity with the mature polypeptide of SEQ ID NO: 1 (Bovine chymosin).

Said in other words and in general—a herein relevant isolated chymosin polypeptide variant may comprise alterations (e.g. substitutions) in other positions than the positions of e.g. the first aspect herein.

As discussed above—in working examples herein were made variants using the polypeptide of SEQ ID NO: 2 (Camel) as parent polypeptide—such variant may herein be termed camel chymosin variant.

Accordingly, in a preferred embodiment—the parent polypeptide has at least 90% sequence identity with the mature polypeptide of SEQ ID NO: 2 (Camel chymosin), more preferably the parent polypeptide has at least 95% sequence identity with the mature polypeptide of SEQ ID NO: 2 (Camel chymosin) and even more preferably the parent polypeptide has at least 97% sequence identity with the mature polypeptide of SEQ ID NO: 2 (Camel chymosin). It may be preferred that the parent polypeptide is the mature polypeptide of SEQ ID NO: 2 (Camel chymosin).

As understood by the skilled person in the present context—a parent polypeptide that has at least 90% sequence identity with the mature polypeptide of SEQ ID NO: 2 (Camel) is still within the SEQ ID NO: 1 (Bovine) based sequence identity requirement of point (ii) of first aspect herein—i.e. it will be a parent polypeptide that has at least 65% sequence identity with the mature polypeptide of SEQ ID NO: 1 (bovine chymosin).

An Isolated Variant of Bovine Chymosin:

As discussed above—in working examples herein were made variants using the polypeptide of SEQ ID NO: 1 (Bovine) as parent polypeptide—such variant may herein be termed bovine chymosin variants.

As discussed above—the third aspect accordingly relates to an isolated chymosin polypeptide variant comprising:
(a): an alteration at one or more positions in a parent polypeptide having chymosin activity, wherein the alteration is comprising a substitution, a deletion or an insertion in at least one amino acid position corresponding to any of positions 70; 75; 77; 79; 90; 102; 103; 108; 114; 117; 120; 124; 134; 154; 156; 163; 212; 222; 223; 224; 238; 246; 256; 261; K279V; L280; F281; R300D,E,S,T,N,Q,C,U,G,P,A,V,I,L,M,F,Y,W; G309; R312D,E,S,T,N,Q,C,U,G,P,A,V,I,L,M,F,Y,W; 320; 324; D325Q; 326; 331; 336; 346; 361; 367 and 379; and
(b): wherein the variant has chymosin activity;
and wherein:
(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and
(ii): the parent polypeptide has at least 90% sequence identity with the mature polypeptide of SEQ ID NO: 1 (bovine chymosin), which is from amino acid position 59 to amino acid position 381 of SEQ ID NO: 1; and
(iii): the isolated variant polypeptide has less than 100% sequence identity with the mature polypeptide of SEQ ID NO: 1 (bovine chymosin);
and with the proviso that the isolated chymosin polypeptide variant is NOT a specific variant selected from the group consisting of:
Q246E+G309D+S329P+D337E;
R125Q+G128N+H204R+Q246E+S284T;
Y185F+R213Q+Q246E;
V261A+V263I+G309W+L311I+Y326F;
G128D+L188I+Y326F;
G128N+R312S+S313Y+Y326F;
G128N+R312S+S313Y+Y326F; and
D117N+V261A+R312S;
D216S+L224V+V263I+F281V+G309D
Y79S+L224V+L311I and
R119S+L224V+T297S.

The above described definitions and preferred embodiments are also relevant for this aspect.

Preferably, an isolated bovine chymosin polypeptide variant as described herein is a variant, wherein the variant has a chymosin activity giving a higher C/P ratio as compared to the C/P ratio of bovine chymosin comprising the mature polypeptide of SEQ ID NO: 1.

In a preferred embodiment—the parent polypeptide has at least 92% sequence identity with the mature polypeptide of SEQ ID NO: 1 (bovine chymosin), more preferably the parent polypeptide has at least 95% sequence identity with the mature polypeptide of SEQ ID NO: 1 (bovine chymosin) and even more preferably the parent polypeptide has at least 97% sequence identity with the mature polypeptide of SEQ ID NO: 1 (bovine chymosin). It may be preferred that the parent polypeptide is the mature polypeptide of SEQ ID NO: 1 (bovine chymosin).

As understood by the skilled person in the present context—an isolated chymosin variant may comprise alterations (e.g. substitutions) in other amino acid positions than given above.

For instance, a bovine chymosin variant with e.g. 5-10 alterations (e.g. substitutions) as compared to wildtype bovine chymosin polypeptide of SEQ ID NO: 1 will still be a parent polypeptide that has at least 95% sequence identity with the mature polypeptide of SEQ ID NO: 1 (Bovine chymosin).

It may be preferred that the isolated bovine chymosin variant comprises less than 30 amino acid alterations (e.g. substitutions) as compared to the mature polypeptide of SEQ ID NO: 1 (bovine chymosin) or it may be preferred that the isolated bovine chymosin variant comprises less than 20 amino acid alterations (e.g. substitutions) as compared to the mature polypeptide of SEQ ID NO: 1 (bovine chymosin) or it may be preferred that the isolated bovine chymosin variant comprises less than 10 amino acid alterations (e.g. substitutions) as compared to the mature polypeptide of SEQ ID NO: 1 (bovine chymosin) or it may be preferred that the isolated bovine chymosin variant comprises less than 5 amino acid alterations (e.g. substitutions) as compared to the mature polypeptide of SEQ ID NO: 1 (bovine chymosin).

As understood by the skilled person in the present context—the term "the isolated variant polypeptide has less than 100% sequence identity with the mature polypeptide of SEQ ID NO: 1 (bovine chymosin)" of point (iii) above relates to that the herein described isolated bovine chymosin variant shall of course not have a polypeptide sequence that is 100% identical to the public known wild-type bovine chymosin sequence of SEQ ID NO: 1.

A preferred embodiment relates to an isolated bovine chymosin polypeptide variant, wherein the alteration comprises a substitution, a deletion or an insertion in at least one amino acid position corresponding to any of positions of the third aspect.

It may be preferred that at least one alteration is a substitution—i.e. a herein relevant preferred embodiment relates to an isolated chymosin polypeptide variant, wherein the alteration is comprising a substitution in at least one amino acid position corresponding to any of positions of the third aspect.

Preferably, the substitution is L70M; F75Y; K77T; Y79S; V90L; D102N; I103V; N108D; D117N; F114Y; K120Q; F124Y; H134Q; I154L; D156V; L163E; S212A; M223E; L224V; L238I; Q246E; V256I; V261A; K279V; L280I; F281A; R300D,E,S,T,N,Q; R312D,E,S,T,N,Q; E320T; R324V; D325Q; Y326F; K336D,E,S,T,N,Q,C,U,G,P,A,V,I,L,M,F,Y,W; S331Y; Q346E; I361L; V367I; or K379P.

Preferably, the substitution is Q246E; K279V; R300Q; R312S; Y326F or K336D,E,S,T,N,Q, wherein a preferred K336 substitution is K336Q.

In a preferred embodiment, the substitution is:
H134Q+Q246E+Y326F;
D117N+L280I+G309D;
H134Q+D156V+G309D;
D156V+Q246E+L280I;
D117N+H134Q+L280I;
D156V+G309D+Y326F;
D117N+D156V+D325M;
L280I+D325M+Y326F;
D117N+Q246E+Y326F;
D117N+H134Q+D325M;

N310Q+N349Q+K279V;
R300Q+N307D;
N307D+G309D;
N307D+R312S;
R300Q+K336Q;
N307D+K336Q;
G309D+R312S;
R300Q+N307D+G309D+R312S+K336Q;
N158Q+N349Q+R300Q+N307D+G309D+R312S+K336Q;
L280I+G309D+S331Y+T342S+D325Q;
L280I+G309D+L224V+E320T+T235S;
L280I+G309W+K77T+R324I;
L280I+G309D+H134Q+V213F+F281A;
L280I+G309D+V213F+E320T+V90L;
L280I+G309D+Q220S+L224V+H134Q;
L280I+G309W+L238I+T342S;
L280I+G309W+F75Y+Y79S;
L280I+G309D+F75Y+S331Y+Q346E;
L280I+G309D+L224V+I103V+L238I;
L280I+G309D+F124Y+Q346E+I154L;
L280I+G309D+I154L+V261A+V367I;
L280I+G309D+Y79S+L224V+S212A;
L280I+G309D+L70M+T342S;
L280I+G309D+H134Q+M223E+L70M;
L280I+G309D+Y79S+T342S+I154L;
L280I+G309D+Y79S+I103V+F281A;
L280I+G309D+V256I+V261A+K379P;
L280I+G309D+Q346E+K77T+T235S;
L280I+G309D+H239N+R324I+D325Q;
L280I+G309D+H134Q+V213F+F281A;
L280I+G309D+Y326F+L70M+D325Q;
L280I+G309D+H134Q+M223E+L70M;
L280I+G309W+S212A+V261A;
L280I+G309D+S331Y+L224V+Y326F;
L280I+G309D+K120Q+M223E+H239N;
L280I+G309D+H239N+R324I+D325Q;
L280I+G309W+L238I+T342S;
L280I+G309D+V213F+E320T+V90L;
L280I+G309D+L70M+T342S;
L280I+G309D+H134Q+V213F+F281A;
L280I+G309D+Y79S+L224V+S212A;
L280I+G309D+S331Y+L224V+Y326F;
L280I+G309D+H134Q+M223E+L70M;
L280I+G309W+L238I+T342S;
L280I+G309D+V213F+E320T+V90L; or
L280I+G309W+S212A+V261A.

In a more preferred embodiment, the substitution is wherein the substitution is:
D117N+L280I+G309D;
L280I+D325M+Y326F;
D117N+Q246E+Y326F;
R300Q+N307D+G309D+R312S+K336Q; or
N158Q+N349Q+R300Q+N307D+G309D+R312S+K336Q.

An Isolated Variant of Camel Chymosin:

As discussed above—in working examples herein were made variants using the polypeptide of SEQ ID NO: 2 (camel chymosin) as parent polypeptide—such variant may herein be termed camel chymosin variant.

As discussed above—the fourth aspect accordingly relates to an isolated chymosin polypeptide variant comprising:

(a): an alteration at one or more positions in a parent polypeptide having chymosin activity, wherein the alteration is comprising a substitution, a deletion or an insertion in at least one amino acid position corresponding to any of positions 70; 75; 77; 79; 90; 102; 103; 108; 114; 117; 120; 124; 134; 154; 156; 163; 212; 223; 224; 238; 246; 256; 261;

K279V; L280; F281; R300D,E,S,T,N,Q,C,U,G,P,A,V,I,L,M, F,Y,W; G309; R312D,E,S,T,N,Q,C,U,G,P,A,V,I,L,M,F,Y,W; 320; 324; D325Q; 326; 331; 336; 346; 361; 367 and 379; and
(b): wherein the variant has chymosin activity;
and wherein:
(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and
(ii): the parent polypeptide has at least 90% sequence identity with the mature polypeptide of SEQ ID NO: 2 (Camel chymosin), which is from amino acid position 59 to amino acid position 381 of SEQ ID NO: 2; and
(iii): the isolated variant polypeptide has less than 100% sequence identity with the mature polypeptide of SEQ ID NO: 2 (camel chymosin);
and with the proviso that the isolated chymosin polypeptide variant is NOT a specific variant selected from the group consisting of:
Q246E+G309D+S329P+D337E;
R125Q+G128N+H204R+Q246E+S284T;
Y185F+R213Q+Q246E;
V261A+V263I+G309W+L311I+Y326F;
G128D+L188I+Y326F;
G128N+R312S+S313Y+Y326F;
G128N+R312S+S313Y+Y326F;
D117N+V261A+R312S;
D216S+L224V+V263I+F281V+G309D;
Y79S+L224V+L311I; and
R119S+L224V+T297S.

The above described definitions and preferred embodiments are also relevant for this aspect.

Preferably, an isolated camel chymosin polypeptide variant as described herein is a variant, wherein the variant has a chymosin activity giving a higher C/P ratio as compared to the C/P ratio of camel chymosin comprising the mature polypeptide of SEQ ID NO: 2.

In a preferred embodiment—the parent polypeptide has at least 92% sequence identity with the mature polypeptide of SEQ ID NO: 2 (camel chymosin), more preferably the parent polypeptide has at least 95% sequence identity with the mature polypeptide of SEQ ID NO: 2 (camel chymosin) and even more preferably the parent polypeptide has at least 97% sequence identity with the mature polypeptide of SEQ ID NO: 2 (camel chymosin). It may be preferred that the parent polypeptide is the mature polypeptide of SEQ ID NO: 2 (Camel chymosin).

As understood by the skilled person in the present context—an isolated chymosin variant may comprise alterations (e.g. substitutions) in other amino acid positions than given above.

For instance, a camel chymosin variant with e.g. 5-10 alterations (e.g. substitutions) as compared to wildtype camel chymosin polypeptide of SEQ ID NO: 2 will still be a parent polypeptide that has at least 95% sequence identity with the mature polypeptide of SEQ ID NO: 2 (camel chymosin).

It may be preferred that the isolated camel chymosin variant comprises less than 30 amino acid alterations (e.g. substitutions) as compared to the mature polypeptide of SEQ ID NO: 2 (camel chymosin) or it may be preferred that the isolated camel chymosin variant comprises less than 20 amino acid alterations (e.g. substitutions) as compared to the mature polypeptide of SEQ ID NO: 2 (camel chymosin) or it may be preferred that the isolated camel chymosin variant comprises less than 10 amino acid alterations (e.g. substitutions) as compared to the mature polypeptide of SEQ ID NO: 2 (camel chymosin) or it may be preferred that the isolated camel chymosin variant comprises less than 5 amino acid alterations (e.g. substitutions) as compared to the mature polypeptide of SEQ ID NO: 2 (camel chymosin).

As understood by the skilled person in the present context—the term "the isolated variant polypeptide has less than 100% sequence identity with the mature polypeptide of SEQ ID NO: 2 (camel chymosin)" of point (iii) above relates to that the herein described isolated camel chymosin variant shall of course not have a polypeptide sequence that is 100% identical to the public known wild-type camel chymosin sequence of SEQ ID NO: 2.

A preferred embodiment relates to an isolated camel chymosin polypeptide variant, wherein the alteration comprises a substitution, a deletion or an insertion in at least one amino acid position corresponding to any of positions of the fourth aspect.

It may be preferred that at least one alteration is a substitution—i.e. a herein relevant preferred embodiment relates to an isolated chymosin polypeptide variant, wherein the alteration is comprising a substitution in at least one amino acid position corresponding to any of positions of the fourth aspect.

Preferably, the substitution is L70M; F75Y; K77T; Y79S; V90L; D102N; I103V; K120Q; F124Y; I154L; L163E; S212A; M223E; L224V; L238I; Q246E; V256I; V261A; K279V; R300D,E,S,T,N,Q; R312D,E,S,T,N,Q; E320T; R324V; Y326F; K336D,E,S,T,N,Q,C,U,G,P,A,V,I,L,M,F,Y, W; S331Y; Q346E; I361L; V367I; or K379P.

Preferably, the substitution is Q246E; K279V; R300Q; R312S; Y326F or K336D,E,S,T,N,Q, wherein a preferred K336 substitution is K336Q.

In a preferred embodiment, the substitution is:
H134Q+Q246E+Y326F;
D117N+L280I+G309D;
H134Q+D156V+G309D;
D156V+Q246E+L280I;
D117N+H134Q+L280I;
D156V+G309D+Y326F;
D117N+D156V+D325M;
L280I+D325M+Y326F;
D117N+Q246E+Y326F;
D117N+H134Q+D325M;
N310Q+N349Q+K279V;
R300Q+N307D;
N307D+G309D;
N307D+R312S;
R300Q+K336Q;
N307D+K336Q;
G309D+R312S;
R300Q+N307D+G309D+R312S+K336Q;
N158Q+N349Q+R300Q+N307D+G309D+R312S+K336Q;
L280I+G309D+S331Y+T342S+D325Q;
L280I+G309D+L224V+E320T+T235S;
L280I+G309W+K77T+R324I;
L280I+G309D+H134Q+V213F+F281A;
L280I+G309D+V213F+E320T+V90L;
L280I+G309D+Q220S+L224V+H134Q;
L280I+G309W+L238I+T342S;
L280I+G309W+F75Y+Y79S;
L280I+G309D+F75Y+S331Y+Q346E;
L280I+G309D+L224V+I103V+L238I;
L280I+G309D+F124Y+Q346E+I154L;
L280I+G309D+I154L+V261A+V367I;

L280I+G309D+Y79S+L224V+S212A;
L280I+G309D+L70M+T342S;
L280I+G309D+H134Q+M223E+L70M;
L280I+G309D+Y79S+T342S+I154L;
L280I+G309D+Y79S+I103V+F281A;
L280I+G309D+V256I+V261A+K379P;
L280I+G309D+Q346E+K77T+T235S;
L280I+G309D+H239N+R324I+D325Q;
L280I+G309D+H134Q+V213F+F281A;
L280I+G309D+Y326F+L70M+D325Q;
L280I+G309D+H134Q+M223E+L70M;
L280I+G309W+S212A+V261A;
L280I+G309D+S331Y+L224V+Y326F;
L280I+G309D+K120Q+M223E+H239N;
L280I+G309D+H239N+R324I+D325Q;
L280I+G309W+L238I+T342S;
L280I+G309D+V213F+E320T+V90L;
L280I+G309D+L70M+T342S;
L280I+G309D+H134Q+V213F+F281A;
L280I+G309D+Y79S+L224V+S212A;
L280I+G309D+S331Y+L224V+Y326F;
L280I+G309D+H134Q+M223E+L70M;
L280I+G309W+L238I+T342S;
L280I+G309D+V213F+E320T+V90L; or
L280I+G309W+S212A+V261A.

In a more preferred embodiment, the substitution is wherein the substitution is:
D117N+L280I+G309D;
L280I+D325M+Y326F;
D117N+Q246E+Y326F;
R300Q+N307D+G309D+R312S+K336Q; or
N158Q+N349Q+R300Q+N307D+G309D+R312S+K336Q.

A Method for Making a Milk Based Product

As discussed above—an isolated chymosin polypeptide variant as described herein may be used according to the art—e.g. to make a milk based product of interest (such as e.g. a cheese product).

As discussed above—an aspect of the invention relates to a method for making a food or feed product comprising adding an effective amount of the isolated chymosin polypeptide variant as described herein to the food or feed ingredient(s) and carrying our further manufacturing steps to obtain the food or feed product.

Preferably, the food or feed product is a milk based product and wherein the method comprises adding an effective amount of the isolated chymosin polypeptide variant as described herein to milk and carrying our further manufacturing steps to obtain the milk based product.

The milk may e.g. be soy milk, sheep milk, goat milk, buffalo milk, yak milk, lama milk, camel milk or cow milk.

The milk based product may e.g. be a fermented milk product, a quark or a cheese.

Aspects/Embodiments Herein—Presented in Claim Format

Herein described aspects and preferred embodiments of the invention may be presented/described in a so-called claim format—this is done below.

1. A method for making an isolated chymosin polypeptide variant comprising the steps:
(a): making an alteration at one or more positions in a parent polypeptide having chymosin activity, wherein the alteration is comprising a substitution, a deletion or an insertion in at least one amino acid position corresponding to any of positions 70; 75; 77; 79; 90; 102; 103; 108; 114; 117; 120; 124; 134; 154; 156; 163; 212; 222; 223; 224; 238; 246; 256; 261; K279V; L280; F281; R300D,E,S,T,N,Q,C,U,G,P,A,V, I,L,M,F,Y,W; G309; R312D,E,S,T,N,Q,C,U,G,P,A,V,I,L,M, F,Y,W; 320; 324; D325Q; 326; 331; 336; 346; 361; 367 and 379; and
(b): producing and isolating the altered polypeptide of step (a) and thereby obtaining the isolated chymosin polypeptide variant, wherein the variant has chymosin activity;
and wherein:
(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and
(ii): the parent polypeptide has at least 65% sequence identity with the mature polypeptide of SEQ ID NO: 1 (bovine chymosin), which is from amino acid position 59 to amino acid position 381 of SEQ ID NO: 1;
and with the proviso that the isolated chymosin polypeptide variant is NOT a specific variant selected from the group consisting of:
Q246E+G309D+S329P+D337E;
R125Q+G128N+H204R+Q246E+S284T;
Y185F+R213Q+Q246E;
V261A+V263I+G309W+L311I+Y326F;
G128D+L188I+Y326F;
G128N+R312S+S313Y+Y326F;
G128N+R312S+S313Y+Y326F;
D117N+V261A+R312S;
D216S+L224V+V263I+F281V+G309D;
Y79S+L224V+L311I; and
R119S+L224V+T297S.

2. The method for making an isolated chymosin polypeptide variant of claim 1, wherein the isolated chymosin polypeptide variant has:
a chymosin activity giving a higher C/P ratio as compared to the C/P ratio of bovine chymosin comprising the mature polypeptide of SEQ ID NO: 1; and
a chymosin activity giving a higher C/P ratio as compared to the C/P ratio of camel chymosin comprising the mature polypeptide of SEQ ID NO: 2.

3. The method for making an isolated chymosin polypeptide variant of any of the preceding claims, wherein the alteration comprises a substitution, a deletion or an insertion in at least one amino acid position corresponding to any of positions of claim 1.

4. The method for making an isolated chymosin polypeptide variant of any of the preceding claims, wherein the alteration comprises a substitution in at least one amino acid position corresponding to any of positions of claim 1.

5. The method for making an isolated chymosin polypeptide variant of claim 4, wherein the substitution is L70M; F75Y; K77T; Y79S; V90L; D102N; I103V; N108D; D117N; F114Y; K120Q; F124Y; H134Q; I154L; D156V; L163E; S212A; S222G; M223E; L224V; L238I; Q246E; V256I; V261A; K279V; L280I; F281A; R300D,E,S,T,N,Q; R312D, E,S,T,N,Q; E320T; R324V; D325Q; Y326F; K336D,E,S,T, N,Q,C,U,G,P,A,V,I,L,M,F,Y,W; S331Y; Q346E; I361L; V367I; or K379P.

6. The method for making an isolated chymosin polypeptide variant of claim 5, wherein the substitution is Q246E; K279V; R300Q; R312S; Y326F or K336D,E,S,T,N,Q.

7. The method for making an isolated chymosin polypeptide variant of claim 6, wherein the substitution is K336Q.

8. The method for making an isolated chymosin polypeptide variant of claim 4, wherein the substitution is:
H134Q+Q246E+Y326F;
D117N+L280I+G309D;

H134Q+D156V+G309D;
D156V+Q246E+L280I;
D117N+H134Q+L280I;
D156V+G309D+Y326F;
D117N+D156V+D325M;
L280I+D325M+Y326F;
D117N+Q246E+Y326F;
D117N+H134Q+D325M;
N310Q+N349Q+K279V;
R300Q+N307D;
N307D+G309D;
N307D+R312S;
R300Q+K336Q;
N307D+K336Q;
G309D+R312S;
R300Q+N307D+G309D+R312S+K336Q;
N158Q+N349Q+R300Q+N307D+G309D+R312S+K336Q;
L280I+G309D+S331Y+T342S+D325Q;
L280I+G309D+L224V+E320T+T235S;
L280I+G309W+K77T+R324I;
L280I+G309D+H134Q+V213F+F281A;
L280I+G309D+V213F+E320T+V90L;
L280I+G309D+Q220S+L224V+H134Q;
L280I+G309W+L238I+T342S;
L280I+G309W+F75Y+Y79S;
L280I+G309D+F75Y+S331Y+Q346E;
L280I+G309D+L224V+I103V+L238I;
L280I+G309D+F124Y+Q346E+I154L;
L280I+G309D+I154L+V261A+V367I;
L280I+G309D+Y79S+L224V+S212A;
L280I+G309D+L70M+T342S;
L280I+G309D+H134Q+M223E+L70M;
L280I+G309D+Y79S+T342S+I154L;
L280I+G309D+Y79S+I103V+F281A;
L280I+G309D+V256I+V261A+K379P;
L280I+G309D+Q346E+K77T+T235S;
L280I+G309D+H239N+R324I+D325Q;
L280I+G309D+H134Q+V213F+F281A;
L280I+G309D+Y326F+L70M+D325Q;
L280I+G309D+H134Q+M223E+L70M;
L280I+G309W+S212A+V261A;
L280I+G309D+S331Y+L224V+Y326F;
L280I+G309D+K120Q+M223E+H239N;
L280I+G309D+H239N+R324I+D325Q;
L280I+G309W+L238I+T342S;
L280I+G309D+V213F+E320T+V90L;
L280I+G309D+L70M+T342S;
L280I+G309D+H134Q+V213F+F281A;
L280I+G309D+Y79S+L224V+S212A;
L280I+G309D+S331Y+L224V+Y326F;
L280I+G309D+H134Q+M223E+L70M;
L280I+G309W+L238I+T342S;
L280I+G309D+V213F+E320T+V90L; or
L280I+G309W+S212A+V261A.

9. The method for making an isolated chymosin polypeptide variant of claim 4, wherein the substitution is:
D117N+L280I+G309D;
L280I+D325M+Y326F;
D117N+Q246E+Y326F;
R300Q+N307D+G309D+R312S+K336Q; or
N158Q+N349Q+R300Q+N307D+G309D+R312S+K336Q.

10. The method for making an isolated chymosin polypeptide variant of any of the preceding claims, wherein the parent polypeptide has at least 75% sequence identity with the mature polypeptide of SEQ ID NO: 1 (bovine chymosin).

11. The method for making an isolated chymosin polypeptide variant of claim 10, wherein the parent polypeptide has at least 95% sequence identity with the mature polypeptide of SEQ ID NO: 1 (bovine chymosin).

12. The method for making an isolated chymosin polypeptide variant of any of claims 1 to 9, wherein the parent polypeptide has at least 95% sequence identity with the mature polypeptide of SEQ ID NO: 2 (Camel chymosin), which is from amino acid position 59 to amino acid position 381 of SEQ ID NO: 2.

13. An isolated chymosin polypeptide variant obtained by the method of any of claims 1 to 12.

14. An isolated chymosin polypeptide variant comprising:
(a): an alteration at one or more positions in a parent polypeptide having chymosin activity, wherein the alteration is comprising a substitution, a deletion or an insertion in at least one amino acid position corresponding to any of positions 70; 75; 77; 79; 90; 102; 103; 108; 114; 117; 120; 124; 134; 154; 156; 163; 212; 222; 223; 224; 238; 246; 256; 261; K279V; L280; F281; R300D,E,S,T,N,Q,C,U,G,P,A,V,I,L,M,F,Y,W; G309; R312D,E,S,T,N,Q,C,U,G,P,A,V,I,L,M,F,Y,W; 320; 324; D325Q; 326; 331; 336; 346; 361; 367 and 379; and
(b): wherein the variant has chymosin activity;
and wherein:
(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and
(ii): the parent polypeptide has at least 90% sequence identity with the mature polypeptide of SEQ ID NO: 1 (bovine chymosin), which is from amino acid position 59 to amino acid position 381 of SEQ ID NO: 1; and
(iii): the isolated variant polypeptide has less than 100% sequence identity with the mature polypeptide of SEQ ID NO: 1 (bovine chymosin);
and with the proviso that the isolated chymosin polypeptide variant is NOT a specific variant selected from the group consisting of:
Q246E+G309D+S329P+D337E;
R125Q+G128N+H204R+Q246E+S284T;
Y185F+R213Q+Q246E;
V261A+V263I+G309W+L311I+Y326F;
G128D+L188I+Y326F;
G128N+R312S+S313Y+Y326F;
G128N+R312S+S313Y+Y326F;
D117N+V261A+R312S;
D216S+L224V+V263I+F281V+G309D
Y79S+L224V+L311I and
R119S+L224V+T297S.

15. The isolated chymosin polypeptide variant of claim 14, wherein the isolated variant has a chymosin activity giving a higher C/P ratio as compared to the C/P ratio of bovine chymosin comprising the mature polypeptide of SEQ ID NO: 1.

16. The isolated chymosin polypeptide variant of any of claims 14 to 15, wherein the parent polypeptide has at least 97% sequence identity with the mature polypeptide of SEQ ID NO: 1 (bovine chymosin).

17. The isolated chymosin polypeptide variant of any of claims 14 to 16, wherein the isolated bovine chymosin variant comprises less than 10 amino acid alterations (e.g. substitutions) as compared to the mature polypeptide of SEQ ID NO: 1 (bovine chymosin).

18. The isolated chymosin polypeptide variant of any of claims 14 to 17, wherein the alteration comprises a substitution, a deletion or an insertion in at least one amino acid position corresponding to any of positions of claim 14.

19. The isolated chymosin polypeptide variant of any of claims 16 to 18, wherein the alteration comprises a substitution in at least one amino acid position corresponding to any of positions of claim 14.

20. The isolated chymosin polypeptide variant of claim 19, wherein the substitution is L70M; F75Y; K77T; Y79S; V90L; D102N; I103V; N108D; D117N; F114Y; K120Q; F124Y; H134Q; I154L; D156V; L163E; S212A; S222G; M223E; L224V; L238I; Q246E; V256I; V261A; K279V; L280I; F281A; R300D,E,S,T,N,Q; G309D,W; R312D,E,S,T,N,Q; E320T; R324V; D325Q; Y326F; K336D,E,S,T,N,Q,C,U,G,P,A,V,I,L,M,F,Y,W; S331Y; Q346E; I361L; V367I; or K379P.

21. The isolated chymosin polypeptide variant of claim 20, wherein the substitution is Q246E; K279V; R300Q; R312S; Y326F or K336D,E,S,T,N,Q.

22. The isolated chymosin polypeptide variant of claim 21, wherein the substitution is K336Q.

23. The isolated chymosin polypeptide variant of claim 19, wherein the substitution is:
H134Q+Q246E+Y326F;
D117N+L280I+G309D;
H134Q+D156V+G309D;
D156V+Q246E+L280I;
D117N+H134Q+L280I;
D156V+G309D+Y326F;
D117N+D156V+D325M;
L280I+D325M+Y326F;
D117N+Q246E+Y326F;
D117N+H134Q+D325M;
N310Q+N349Q+K279V;
R300Q+N307D;
N307D+G309D;
N307D+R312S;
R300Q+K336Q;
N307D+K336Q;
G309D+R312S;
R300Q+N307D+G309D+R312S+K336Q;
N158Q+N349Q+R300Q+N307D+G309D+R312S+K336Q;
L280I+G309D+S331Y+T342S+D325Q;
L280I+G309D+L224V+E320T+T235S;
L280I+G309W+K77T+R324I;
L280I+G309D+H134Q+V213F+F281A;
L280I+G309D+V213F+E320T+V90L;
L280I+G309D+Q220S+L224V+H134Q;
L280I+G309W+L238I+T342S;    L280I+G309W+F75Y+Y79S;
L280I+G309D+F75Y+S331Y+Q346E;
L280I+G309D+L224V+I103V+L238I;
L280I+G309D+F124Y+Q346E+I154L;
L280I+G309D+I154L+V261A+V367I;
L280I+G309D+Y79S+L224V+S212A;
L280I+G309D+L70M+T342S;
L280I+G309D+H134Q+M223E+L70M;
L280I+G309D+Y79S+T342S+I154L;
L280I+G309D+Y79S+I103V+F281A;
L280I+G309D+V256I+V261A+K379P;
L280I+G309D+Q346E+K77T+T235S;
L280I+G309D+H239N+R324I+D325Q;
L280I+G309D+H134Q+V213F+F281A;
L280I+G309D+Y326F+L70M+D325Q;
L280I+G309D+H134Q+M223E+L70M;
L280I+G309W+S212A+V261A;
L280I+G309D+S331Y+L224V+Y326F;
L280I+G309D+K120Q+M223E+H239N;
L280I+G309D+H239N+R324I+D325Q;
L280I+G309W+L238I+T342S;
L280I+G309D+V213F+E320T+V90L;
L280I+G309D+L70M+T342S;
L280I+G309D+H134Q+V213F+F281A;
L280I+G309D+Y79S+L224V+S212A;
L280I+G309D+S331Y+L224V+Y326F;
L280I+G309D+H134Q+M223E+L70M;
L280I+G309W+L238I+T342S;
L280I+G309D+V213F+E320T+V90L; or
L280I+G309W+S212A+V261A.

24. The isolated chymosin polypeptide variant of claim 19, wherein the substitution is:
D117N+L280I+G309D;
L280I+D325M+Y326F;
D117N+Q246E+Y326F;
R300Q+N307D+G309D+R312S+K336Q; or
N158Q+N349Q+R300Q+N307D+G309D+R312S+K336Q.

25. An isolated chymosin polypeptide variant comprising:
(a): an alteration at one or more positions in a parent polypeptide having chymosin activity, wherein the alteration is comprising a substitution, a deletion or an insertion in at least one amino acid position corresponding to any of positions 70; 75; 77; 79; 90; 102; 103; 108; 114; 117; 120; 124; 134; 154; 156; 163; 212; 222; 223; 224; 238; 246; 256; 261; K279V; L280; F281; R300D,E,S,T,N,Q,C,U,G,P,A,V,I,L,M,F,Y,W; G309; R312D,E,S,T,N,Q,C,U,G,P,A,V,I,L,M,F,Y,W; 320; 324; D325Q; 326; 331; 336; 346; 361; 367 and 379; and
(b): wherein the variant has chymosin activity;
and wherein:
(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and
(ii): the parent polypeptide has at least 90% sequence identity with the mature polypeptide of SEQ ID NO: 2 (Camel chymosin), which is from amino acid position 59 to amino acid position 381 of SEQ ID NO: 2; and
(iii): the isolated variant polypeptide has less than 100% sequence identity with the mature polypeptide of SEQ ID NO: 2 (camel chymosin);
and with the proviso that the isolated chymosin polypeptide variant is NOT a specific variant selected from the group consisting of:
Q246E+G309D+S329P+D337E;
R125Q+G128N+H204R+Q246E+S284T;
Y185F+R213Q+Q246E;
V261A+V263I+G309W+L311I+Y326F;
G128D+L188I+Y326F;
G128N+R312S+S313Y+Y326F;
G128N+R312S+S313Y+Y326F;
D117N+V261A+R312S;
D216S+L224V+V263I+F281V+G309D;
Y79S+L224V+L311I; and
R119S+L224V+T297S.

26. The isolated chymosin polypeptide variant of claim 25, wherein the isolated variant has a chymosin activity giving a higher C/P ratio as compared to the C/P ratio of camel chymosin comprising the mature polypeptide of SEQ ID NO: 2.

27. The isolated chymosin polypeptide variant of any of claims 25 to 26, wherein the parent polypeptide has at least 97% sequence identity with the mature polypeptide of SEQ ID NO: 2 (camel chymosin).

28. The isolated chymosin polypeptide variant of any of claims 25 to 26, wherein the isolated camel chymosin variant comprises less than 10 amino acid alterations (e.g. substitutions) as compared to the mature polypeptide of SEQ ID NO: 2 (camel chymosin).

29. The isolated chymosin polypeptide variant of any of claims 25 to 28, wherein the alteration comprises a substitution, a deletion or an insertion in at least one amino acid position corresponding to any of positions of claim 23.

30. The isolated chymosin polypeptide variant of any of claims 25 to 29, wherein the alteration comprises a substitution in at least one amino acid position corresponding to any of positions of positions of claim 23.

31. The isolated chymosin polypeptide variant of claim 30, wherein the substitution is L70M; F75Y; K77T; Y79S; V90L; D102N; I103V; N108D; D117N; F114Y; K120Q; F124Y; H134Q; I154L; D156V; L163E; S212A; S222G; M223E; L224V; D325Q; L238I; Q246E; V256I; V261A; K279V; L280I; F281A; R300D,E,S,T,N,Q; G309D,W; R312D,E,S,T,N,Q; E320T; R324V; Y326F; K336D,E,S,T,N,Q,C,U,G,P,A,V,I,L,M,F,Y,W; S331Y; Q346E; I361L; V367I; or K379P.

32. The isolated chymosin polypeptide variant of claim 31, wherein the substitution is Q246E; K279V; R300Q; R312S; Y326F or K336D,E,S,T,N,Q.

33. The isolated chymosin polypeptide variant of claim 32, wherein the substitution is K336Q.

34. The isolated chymosin polypeptide variant of claim 30, wherein the substitution is:
H134Q+Q246E+Y326F;
D117N+L280I+G309D;
H134Q+D156V+G309D;
D156V+Q246E+L280I;
D117N+H134Q+L280I;
D156V+G309D+Y326F;
D117N+D156V+D325M;
L280I+D325M+Y326F;
D117N+Q246E+Y326F;
D117N+H134Q+D325M;
N310Q+N349Q+K279V;
R300Q+N307D;
N307D+G309D;
N307D+R312S;
R300Q+K336Q;
N307D+K336Q;
G309D+R312S;
R300Q+N307D+G309D+R312S+K336Q;
N158Q+N349Q+R300Q+N307D+G309D+R312S+K336Q;
L280I+G309D+S331Y+T342S+D325Q;
L280I+G309D+L224V+E320T+T235S;
L280I+G309W+K77T+R324I;
L280I+G309D+H134Q+V213F+F281A;
L280I+G309D+V213F+E320T+V90L;
L280I+G309D+Q220S+L224V+H134Q;
L280I+G309W+L238I+T342S;
L280I+G309W+F75Y+Y79S;
L280I+G309D+F75Y+S331Y+Q346E;
L280I+G309D+L224V+I103V+L238I;
L280I+G309D+F124Y+Q346E+I154L;
L280I+G309D+I154L+V261A+V367I;
L280I+G309D+Y79S+L224V+S212A;
L280I+G309D+L70M+T342S;
L280I+G309D+H134Q+M223E+L70M;
L280I+G309D+Y79S+T342S+I154L;
L280I+G309D+Y79S+I103V+F281A;
L280I+G309D+V256I+V261A+K379P;
L280I+G309D+Q346E+K77T+T235S;
L280I+G309D+H239N+R324I+D325Q;
L280I+G309D+H134Q+V213F+F281A;
L280I+G309D+Y326F+L70M+D325Q;
L280I+G309D+H134Q+M223E+L70M;
L280I+G309W+S212A+V261A;
L280I+G309D+S331Y+L224V+Y326F;
L280I+G309D+K120Q+M223E+H239N;
L280I+G309D+H239N+R324I+D325Q;
L280I+G309W+L238I+T342S;
L280I+G309D+V213F+E320T+V90L;
L280I+G309D+L70M+T342S;
L280I+G309D+H134Q+V213F+F281A;
L280I+G309D+Y79S+L224V+S212A;
L280I+G309D+S331Y+L224V+Y326F;
L280I+G309D+H134Q+M223E+L70M;
L280I+G309W+L238I+T342S;
L280I+G309D+V213F+E320T+V90L; or
L280I+G309W+S212A+V261A.

35. The isolated chymosin polypeptide variant of claim 30, wherein the substitution is:
D117N+L280I+G309D;
L280I+D325M+Y326F;
D117N+Q246E+Y326F;
R300Q+N307D+G309D+R312S+K336Q; or
N158Q+N349Q+R300Q+N307D+G309D+R312S+K336Q.

36: A method for making a food or feed product comprising adding an effective amount of the isolated chymosin polypeptide variant according to any of claims 14 to 35 to the food or feed ingredient(s) and carrying our further manufacturing steps to obtain the food or feed product.

37: The method for making a food or feed product of claim 35, wherein the product is a milk based product and wherein the method comprises adding an effective amount of the isolated chymosin polypeptide variant according to any of claims 14 to 36 to milk and carrying our further manufacturing steps to obtain the milk based product.

38: The method for making a milk based product of claim 37, wherein the milk is soy milk, sheep milk, goat milk, buffalo milk, yak milk, lama milk, camel milk or cow milk.

39: The method for making a milk based product of any of claims 36 to 38, wherein the milk based product is a fermented milk product, a quark or a cheese.

EXAMPLES

Example 1: Alignment and Numbering of Chymosin Protein Sequences and Variant Sequences Chymosin protein sequences were aligned using the ClustalW algorithm as provided by the EBI (EBI, tools, multiple sequence alignment, CLUSTALW", http://www.ebi.ac.uk/Tools/msa/clustalw2/) and as described in Larkin M A, Blackshields G, Brown N P, Chenna R, McGettigan P A, McWilliam H, Valentin F, Wallace I M, Wilm A, Lopez R, Thompson J D, Gibson T J, Higgins D G (2007). Bioinformatics 23(21), 2947-2948.

ClustalW2 settings for multiple sequence alignments were Protein weight Matrix=BLOSUM, GAP open=10, GAP EXTENSION=0.05, GAP DISTANCES=8, No End Gaps, ITERATION=none, NUMITER=1, CLUSTERING=NJ As a reference sequence the bovine chymosin B prepro-chymosin was used (Genbank accession number P00794—disclosed herein as SEQ ID NO: 1), where the N-terminal Methionin has number 1 (MRCL . . . ) (SEQ ID NO: 7) and the C-terminal Isoleucin (in the protein sequence . . . LAKAI) (SEQ ID NO: 8) has number 381, Variants were aligned against the bovine B pre-pro-chymosin and residues were numbered according to the corresponding bovine chymosin residue.

Example 2: Design of Chymosin Variants

Chymosin variants were designed using different strategies.

When there is referred to camel chymosin there is referred to camel chymosin comprising the polypeptide of SEQ ID NO: 2 herein.

Camel chymosin of SEQ ID NO: 2 may be seen as a herein relevant parent polypeptide having chymosin activity used to make camel chymosin variants thereof.

When there is referred to bovine chymosin there is referred to bovine chymosin comprising the polypeptide of SEQ ID NO: 1 herein.

Bovine chymosin of SEQ ID NO: 1 may be seen as a herein relevant parent polypeptide having chymosin activity used to make bovine chymosin variants thereof.

Variants of camel chymosin were designed based on an alignment of a large set of public known aspartic protease sequences having an identity of 25% or more compared to bovine chymosin B.

Variations were generally introduced in hypervariable regions, while conserved regions were not changed. Multiple variations were introduced in each variant construct, ensuring that each single mutation was present in multiple variant constructs (for discussion of results—see example 6 below).

Variants of bovine chymosin were designed based on a comparison of bovine and camel chymosin. Bovine residues were e.g. changed to the camel counterpart (for discussion of results—see example 7 below).

Example 3: Preparation of Chymosin Variant Enzyme Material

All chymosin variants were synthesized as synthetic genes and cloned into a fungal expression vector corresponding essentially to pGAMpR-C (described in WO02/36752A2)

The vectors were transformed into *E. coli* and plasmid DNA was purified using standard molecular biology protocols, known to the person skilled in the art.

The variant plasmids were individually transformed into an *Aspergillus niger* or *Aspergillus nidulans* strain and protein was produced essentially as described in WO02/36752A2 and purified using standard chromatography techniques.

As known in the art—the skilled person may, based on his common general knowledge, produce and purify chymosin and chymosin variants—such as herein described bovine and camel chymosin variants.

Example 4: Determination of Specific Chymosin Activity 4.1 Determination of Clotting Activity Milk clotting activity was determined using the REMCAT method, which is the standard method developed by the International Dairy Federation (IDF method) Milk clotting activity is determined from the time needed for a visible flocculation of a standard milk substrate prepared from a low-heat, low fat milk powder with a calcium chloride solution of 0.5 g per liter (pH 6.5). The clotting time of a rennet sample is compared to that of a reference standard having known milk-clotting activity and having the same enzyme composition by IDF Standard 110B as the sample. Samples and reference standards were measured under identical chemical and physical conditions. Variant samples were adjusted to approximately 3 IMCU/ml using an 84 mM acetic acid pH 5.5 buffer. Hereafter, 200 µl enzyme was added to 10 ml preheated milk (32° C.) in a glass test tube placed in a water bath, capable of maintaining a constant temperature of 32° C.±1° C. under constant stirring.

The total milk-clotting activity (strength) of a rennet was calculated in International Milk-Clotting Units (IMCU) per ml relative to a standard having the same enzyme composition as the sample according to the formula:

$$\text{Strength in } IMCU/\text{ml} = \frac{Sstandard \times Tstandard \times Dsample}{Dstandard \times Tsample}$$

Sstandard: The milk-clotting activity of the international reference standard for rennet.
Tstandard: Clotting time in seconds obtained for the standard dilution.
Dsample: Dilution factor for the sample
Dstandard: Dilution factor for the standard
Tsample: Clotting time in seconds obtained for the diluted rennet sample from addition of enzyme to time of flocculation For clotting activity determination of camel variant evaluation in Example 9, the pIMCU method was used instead of the REMCAT method. As compared to REMCAT, flocculation time of chymosin variants in the pIMCU assay was determined by OD measurements in 96-well microtiter plates at 800 nm in a UV/VIS plate reader. A standard curve of various dilutions of a reference standard with known clotting strength was recorded on each plate. Samples were prepared by diluting enzyme in 84 mM acetate buffer, 0.1% triton X-100, pH 5.5. Reaction at 32° C. was started by adding 250 uL of a standard milk substrate containing 4% (w/w) low-heat, low fat milk powder and 7.5% (w/w) calcium chloride (pH 6.5) to 25 uL enzyme sample. Milk clotting activity of chymosin variants in International Milk-Clotting Units (IMCU) per ml was determined based on sample flocculation time relative to the standard curve.

4.2 Determination of Total Protein Content

Total protein content was determined using the Pierce BCA Protein Assay Kit from Thermo Scientific following the instructions of the providers.

4.3 Calculation of Specific Clotting Activity

Specific clotting activity (IMCU/mg total protein) was determined by dividing the clotting activity (IMCU/ml) by the total protein content (mg total protein per ml).

Example 5: Determination of Proteolytic Activity

General proteolytic activity was measured using fluorescently labelled Bodipy-FL casein as a substrate (EnzChek; Molecular Bioprobes, E6638). Casein derivatives heavily labeled with pH-insensitive green-fluorescent Bodipy-FL result in almost complete quenching of the conjugate's fluorescence. Protease catalyzed hydrolysis releases fluorescent Bodipy-FL. This method is very sensitive which was essential for this experiment as CHYMAX M has the lowest general proteolytical activity of all coagulants known to date.

The assay was conducted in a 0.2 M phosphate buffer adjusted to the desired pH at a final substrate concentration of 0.04 mg/ml. Prior to mixing 1 part of substrate with 1 part of enzyme, both prepared in the phosphate buffer, all enzyme variants where normalized to 50 IMCU/ml (according to Example 4). The substrate and enzyme were mixed in a 96-well Nunc Fluoro microtiter plates, sealed and incubated at 32° C. for 60 min. After incubation the sealing was removed and the fluorescence recorded in a fluorimeter. For variants evaluated in Examples 9 and 10, 1 part of substrate was mixed with 1 part of non-normalized enzyme samples in 386-well Nunc Fluoro microtiter plates and the fluorescence was continuously recorded in a fluorimeter at 32 C for 10 hours. Slopes of the linear part of fluorescence increase were used to determine general proteolytic activity.

Example 6: Evaluation of Camel Chymosin Variants

For all variants the specific clotting activity (IMCU/mg of total protein) was determined at pH 6.5 according to Example 4 and the proteolytical activity was determined according to example 5 at pH 6.5 The C/P ratio was determined for all variants at pH 6.5 by dividing the specific clotting activity (IMCU/mg) with the proteolytical activity.

As a reference the camel wildtype gene was included.
Variants with Multiple Substitutions
It can be concluded that there are clear combinatorial effects, where different substitutions have an effect on the respective effects.

|   |   | IMCU/mg | Proteol | C/P |
|---|---|---|---|---|
| 1 | H134Q, Q246E, Y326F | 104% | 211% | 49% |
| 2 | D117N, L280I, G309D | 122% | 66% | 185% |
| 3 | H134Q, D156V, G309D | 117% | 179% | 66% |
| 4 | D156V, Q246E, L280I | 105% | 199% | 53% |
| 5 | D117N, H134Q, L280I | 67% | 683% | 10% |
| 6 | D156V, G309D, Y326F | 100% | 115% | 87% |
| 8 | D117N, D156V, D325M | 127% | 457% | 28% |
| 9 | L280I, D325M, Y326F | 113% | 94% | 121% |
| 10 | D117N, Q246E, Y326F | 127% | 121% | 105% |
| 11 | D117N, H134Q, D325M | 134% | 192% | 69% |
| Ref | camel | 100% | 100% | 100% |

It can be concluded that variants 1, 2, 3, 4, 8, 9, 10 and 11 have a higher specific milk clotting activity, with variants 2, 8, 10 and 11 having the strongest improvement It can be concluded that variants 2 and 9 have a reduced proteolytical activity.

It can be concluded that variants 2, 9 and 10 have an increased C/P ratio.

Based on this variant 2 is the most preferred variant, while variants 9 and 10 also show preferred characteristics.
Individual Mutations As all variants included multiple mutations, the data of the ranked variants were investigated in more details using statistical methods and 3D structure analysis, to determine the individual amino acid changes that have a positive or negative effect.

The effects of the individual amino acid changes can be summarized as follows but depend much upon the other amino acid changes in the different variants.

Based on these the preferred mutations are D117N, Q246E, G 309D, Y326F and L280I.

|   | C | P | C/P |   |
|---|---|---|---|---|
| H134Q | + | -- | -- | Exposed lobe |
| Q246E | + | -- | - | Backbone |
| Y326F | + | - | +/- | Backbone |
| D117N | ++ | -- | - | Backbone lobe |
| L280I | + | +/- | +/- | In cleft |
| G309D | + | -- | +/- | Outside small lobe |
| D156V | + | -- | -- | Backbone |
| D325M | ++ | -- | -- | Backbone |

The term "+" refers to a positive amino acid exchange— i.e. "++" is more positive than "+".

The term "−" refers to a negative amino acid exchange— i.e. "−−" is more negative than "−".

The term "positive" refers to a positive effect on the cheese making properties of the variants, i.e. improved clotting activity ("C") and increased C/P ratio are considered to be positive ("+" or "++") while increased general proteolytical activity ("P") is considered to be a negative property ("−" or "−−"). The qualification "+/−" indicates a relatively neutral effect The descriptions of the right column of the table relates to where the individual mutations are situated in the 3D structure of camel chymosin. The 3D structure of camel chymosin is publicly available.
Conclusions:

The results above demonstrate that following individual mutations in camel chymosin were preferred (i.e. with improved C/P ratio as compared to camel wildtype chymosin): D117N, Q246E, G 309D, Y326F, L280I.

The results above demonstrate that following multiple substitutions/mutations in camel chymosin were preferred (i.e. with improved C/P ratio as compared to camel wildtype chymosin):
D117N+L280I+G309D;
L280I+D325M+Y326F;
D117N+Q246E+Y326F.

Example 7: Evaluation of Camel and Bovine Chymosin Variants

For all variants the specific clotting activity (IMCU/mg of total protein) was determined at pH 6.5 according to Example 4, while the general or aspecific proteolytical activity was determined as described in example 5.

The C/P ratio was determined for all variants at pH 6.5 by dividing the specific clotting activity (IMCU/mg) with the proteolytical activity.

As a reference a camel wildtype gene was included.

For better comparison all variants were made in a background that did not have active N-glycosylation sites, the so called Ugly variants. These were made by changing the N in the two potential N-glycosylation sites into a Q.

For further results, see FIG. 3.
Description of the Variants

In variant J2, K279 was replaced by V in bovine non-glycosylated chymosin

In variant J32, the flap region from bovine non-glycosylated chymosin was replaced by the flap region from Pepsin.

In variant J72, the negative patch from bovine chymosin was used to replace the corresponding regions in camel chymosin. In variant J44, R300 was replaced in camel chymosin by Q, the corresponding amino acid in bovine chymosin. This mutation is also found in variant J72.

|  |  |  | Relative to camel | | |
|---|---|---|---|---|---|
|  |  |  | RemCat | Prot | C/P |
| J2 | BovUgly | N310Q, N349Q, K279V | 54% | 227% | 24% |
| J22 | BovUgly | Pepsin positive patch | 15% | 115% | 13% |
| J32 | BovUgly | K279V, L80I, K129E, P130T, H134T, Q141T, V171F, E191S, Y192G, N310Q, N349Q | 63% | 63% | 10% |
| J44 | CamUGly | R300Q | 123% | 114% | 108% |
| J72 | CamUgly | N158Q, N349Q, R300Q, N307D, G309D, R312S, K336Q | 125% | 58% | 215% |
| CamUgly | Camel | N158Q, N349Q | 100% | 98% | 102% |
| BovUgly | Bovine | N310Q, N349Q | 40% | 208% | 19% |
| Camel |  | N/A | 100% | 100% | 100% |

Conclusions:

Mutation of the Lysin at position 279 of bovine chymosin resulted in a variant that showed comparable proteolytical activity and an increased specific clotting activity as compared to bovine chymosin (variant J2). Accordingly, it can be concluded that Valine at position 279 is the preferred amino acid.

The effect of glycosylation of Camel chymosin on the cheese making properties is neglectible. Comparison of the unglycosylated camel variant with the wild-type camel chymosin indicates no significant changes. However, introduction of the negative patch reason from bovine chymosin in camel chymosin (variant J72) shows a positive effect on the specific clotting activity, while the general proteolytical activity is approximately 2 fold reduced, resulting in a doubling of the C/P ratio. Introduction of the single mutation R300Q from this patch (variant J44) shows a similar positive effect on clotting activity as seen for variant J72. Q is concluded to be the preferred amino acid in position 300.

The negative patch region in bovine chymosin is expected to have an important effect for positioning of the enzyme outward the correct cleavage site, thus improving the enzymes specificity. The effect is expected to be mostly charge related, i.e. any change that increases the negative charge in this reason will result in increased specificity.

Below is shown an alignment of the negative charged region of bovine and camel chymosin. Only charged residues are indicated.

RxxxxxxNxGxxRxxxxxxxxxxxxxxxxxxxxxxK (SEQ ID NO: 9) Camel
QxxxxxxDxDxxSxxxxxxxxxxxxxxxxxxxxxxQ (SEQ ID NO: 10) Bovine With respect to position numbers and using the Camel as reference the numbering is starting from the right:

R300
N307
G309
R312
K336

Example 8: Evaluation of Camel Variants

A number of different variants, each having multiple substitutions as compared to the wild type camel chymosin, was analyzed.

For all variants the specific clotting activity (IMCU/mg of total protein) was determined at pH 6.5 according to Example 4, while the aspecific proteolytical activity was determined as described in Example 5 by measuring proteolytical activity per 100 IMCU.

As a reference a camel wildtype gene was included.

Analysis of Variants

The variants indicated in the table have an amino acid sequence identical to the camel chymosin gene (indicated by camel wt), except for the variations mentioned for each variant.

Clotting activity is mentioned as IMCU per mg of total protein. Improved clotting activities are indicated with one or more "+" symbols. Proteolytical activity is expressed in artificial units per 100 IMCU. Improved variants, i.e. variants with reduced proteolytical activities, are indicated with one or more "+" symbols. More "+" symbols indicate a stronger improvement. In the "Overall" column "+" symbols indicate variants that have generally improved properties, i.e. a low proteolytical activity with a high clotting activity.

TABLE 1 analysis of camel chymosin variants

|  |  |  |  |  |  | Clotting IMCU/mg | | Proteolytical Au/100 IMCU | | Overall |
|---|---|---|---|---|---|---|---|---|---|---|
| 1 | L280I | G309D | E141S | Q220S | R324I | 196 |  | 161852 |  |  |
| 2 | L280I | G309W | F75Y | Y79S |  | 419 | ++ | 43355 |  |  |
| 3 | L280I | G309D | H134Q | S222G | S331Y | 299 |  | 36409 |  |  |
| 4 | L280I | G309D | K120Q | M223E | H239N | 250 |  | 13642 | +++ |  |
| 5 | L280I | G309D | Q220S | V213F | T342S | 231 |  | 139775 |  |  |
| 6 | L280I | G309D | H134Q | V213F | F281A | 376 | + | 23575 | + |  |
| 7 | L280I | G309D | S331Y | L224V | Y326F | 318 |  | 12257 | ++++ | + |
| 8 | L280I | G309D | Y326F | V241I | E305T | 353 | + | 33477 |  |  |
| 9 | L280I | G309D | S331Y | F124Y | I346L | 338 |  | 37156 |  |  |
| 10 | L280I | G309D | M223E | L224V | L273V | 324 |  | 36425 |  |  |
| 11 | L280I | G309D | H134Q | M223E | L70M | 386 | + | 10664 | ++++ | ++ |
| 12 | L280I | G309D | F75Y | S331Y | Q346E | 418 | ++ | 40393 |  |  |
| 13 | L280I | G309D | L224V | I103V | L238I | 412 | ++ | 50010 |  |  |
| 14 | L280I | G309W | L238I | T342S |  | 420 | +++ | 21087 | + | ++ |
| 15 | L280I | G309D |  | L70M | T342S | 395 | ++ | 22743 | + |  |
| 16 | L280I | G309D | Y79S | L224V | S212A | 403 | ++ | 23684 | + |  |
| 17 | L280I | G309D | V213F | E320T | V90L | 426 | +++ | 21956 | + | ++ |
| 18 | L280I | G309D | L163E | S222G | V261A | 246 |  | 97468 |  |  |
| 19 | L280I | G309W | S212A | V261A |  | 344 |  | 10865 | ++++ | + |
| 20 | L280I | G309D | Q220S | L224V | H134Q | 425 | +++ | 35156 |  |  |
| 21 | L280I | G309W | K77T | R324I |  | 434 | +++ | 45616 |  |  |
| 22 | L280I | G309W | I361L | I103V |  | 324 |  | 32966 |  |  |

TABLE 1-continued analysis of camel chymosin variants

| | | | | | | Clotting IMCU/mg | | Proteolytical Au/100 IMCU | Overall |
|---|---|---|---|---|---|---|---|---|---|
| 23 | L280I | G309D | E141S | R324V | V367I | 360 | + | 77215 | |
| 24 | L280I | G309D | Y79S | L273V | L163E | 317 | | 62132 | |
| 25 | L280I | G309D | I154L | T235S | K379P | 333 | | 93587 | |
| 26 | L280I | G309D | F75Y | T342S | V261A | 361 | + | 108877 | |
| 27 | L280I | G309D | V90L | K379P | V318T | 317 | | 52280 | |
| 28 | L280I | G309D | V256I | V90L | E141S | 289 | | 81720 | |
| 29 | L280I | G309D | I154L | V261A | V367I | 405 | ++ | 59055 | |
| 30 | L280I | G309D | Y326F | L273V | V90L | 312 | | 54833 | |
| 31 | L280I | G309D | H134Q | L163E | V318T | 344 | | 43594 | |
| 32 | L280I | G309D | Y79S | H134Q | Y326F | 337 | | 30815 | |
| 33 | L280I | G309D | Y79S | I103V | F281A | 379 | + | 104307 | |
| 34 | L280I | G309D | V256I | V261A | K379P | 378 | + | 39517 | |
| 35 | L280I | G309D | S331Y | L238I | I154L | 293 | | 60312 | |
| 36 | L280I | G309D | S222G | R324V | I154L | 223 | | 62784 | |
| 37 | L280I | G309D | H239N | F124Y | V90L | 312 | | 55432 | |
| 38 | L280I | G309D | H239N | R324I | D325Q | 377 | + | 17261 | ++ |
| 39 | L280I | G309W | K120Q | V367I | | 354 | | 75440 | |
| 40 | L280I | G309D | Y326F | L70M | 9325Q | 373 | + | 72792 | |
| 41 | L280I | G309D | L224V | E320T | T235S | 446 | +++ | 32453 | |
| 42 | L280I | G309D | S331Y | T342S | D325Q | 475 | ++++ | 70103 | |
| 43 | L280I | G309D | F124Y | Q346E | I154L | 410 | ++ | 33586 | |
| 44 | L280I | G309D | V261A | R324V | F281A | 198 | | 34974 | |
| 45 | L280I | G309D | I361L | S212A | V318T | 343 | | 64876 | |
| 46 | L280I | G309D | Y79S | T342S | I154L | 382 | + | 122413 | |
| 47 | L280I | G309D | Q346E | K77T | T235S | 377 | + | 34716 | |
| 48 | L280I | G309D | K120Q | Y326F | K77T | 264 | | 46463 | |
| Camel wt | | | | | | 366 | + | 15.664 | +++ |
| Bovine wt | | | | | | 208 | | 62.662 | |

High specific clotting activity is essential for a good milk clotting enzymes. In total 21 variants with an increased specific clotting activity, relative to the camel chymosin, were identified and included in Table 2 below.

TABLE 2

Camel chymosin variants with increased Clotting activity

| | | | | | | Clotting | | Proteolytical | Overall |
|---|---|---|---|---|---|---|---|---|---|
| 42 | L280I | G309D | S331Y | T342S | D325Q | 475 | ++++ | 70.103 | |
| 41 | L280I | G309D | L224V | E320T | T235S | 446 | +++ | 30.953 | |
| 21 | L280I | G309W | K77T | R324I | | 434 | +++ | 45.616 | |
| 17 | L280I | G309D | V213F | E320T | V90L | 426 | +++ | 21.956 | + | ++ |
| 20 | L280I | G309D | Q220S | L224V | H134Q | 425 | +++ | 35.156 | |
| 14 | L280I | G309W | L238I | T342S | | 420 | +++ | 21.087 | + | ++ |
| 2 | L280I | G309W | F75Y | Y79S | | 419 | ++ | 43.355 | |
| 12 | L280I | G309D | F75Y | S331Y | Q346E | 418 | ++ | 40.393 | |
| 13 | L280I | G309D | L224V | I103V | L238I | 412 | ++ | 50.010 | |
| 43 | L280I | G309D | F124Y | Q346E | I154L | 410 | ++ | 33.586 | |
| 29 | L280I | G309D | I154L | V261A | V367I | 405 | ++ | 59.055 | |
| 16 | L280I | G309D | Y79S | L224V | S212A | 403 | ++ | 23.684 | + |
| 15 | L280I | G309D | | L70M | T342S | 395 | ++ | 22.743 | + |
| 11 | L280I | G309D | H134Q | M223E | L70M | 386 | + | 10.664 | ++++ | ++ |
| 46 | L280I | G309D | Y79S | T342S | I154L | 382 | + | 122.413 | |
| 33 | L280I | G309D | Y79S | I103V | F281A | 379 | + | 104.307 | |
| 34 | L280I | G309D | V256I | V261A | K379P | 378 | + | 39.517 | |
| 47 | L280I | G309D | Q346E | K77T | T235S | 377 | + | 34.716 | |
| 38 | L280I | G309D | H239N | R324I | D325Q | 377 | + | 17.261 | ++ |
| 6 | L280I | G309D | H134Q | V213F | F281A | 376 | + | 23.575 | + |
| 40 | L280I | G309D | Y326F | L70M | D325Q | 373 | + | 72.792 | |
| Camel wt | | | | | | 366 | + | 15.664 | +++ |

Reduced proteolytical activity is a perquisite for a good milk clotting enzymes. In total 10 variants with a reduced proteolytical activity, relative to the camel chymosin, were identified (see Table 3 below).

TABLE 3

Camel chymosin variants with reduced proteolytical activity

| | | | | | | Clotting | | Proteolytical | | Overall |
|---|---|---|---|---|---|---|---|---|---|---|
| 11 | L280I | G309D | H134Q | M223E | L70M | 386 | + | 10.664 | ++++ | ++ |
| 19 | L280I | G309W | S212A | V261A | | 344 | | 10.865 | ++++ | + |
| 7 | L280I | G309D | S331Y | L224V | Y326F | 318 | | 12.257 | ++++ | + |
| 4 | L280I | G309D | K120Q | M223E | H239N | 250 | | 13.642 | +++ | |
| 38 | L280I | G309D | H239N | R324I | D325Q | 377 | + | 17.261 | ++ | |
| 14 | L280I | G309W | L238I | T342S | | 420 | +++ | 21.087 | + | ++ |
| 17 | L280I | G309D | V213F | E320T | V90L | 426 | +++ | 21.956 | + | ++ |
| 15 | L280I | G309D | | L70M | T342S | 395 | ++ | 22.743 | + | |
| 6 | L280I | G309D | H134Q | V213F | F281A | 376 | + | 23.575 | + | |
| 16 | L280I | G309D | Y79S | L224V | S212A | 403 | ++ | 23.684 | + | |
| Camel wt | | | | | | 366 | + | 15.664 | +++ | |

Based on an overall analysis five variants were identified that had improved properties for both milk clotting and proteolytical activities. These five variants are indicated in table 4 below.

TABLE 4

Camel chymosin variants with increased clotting activity and decreased proteolytical activity

| | | | | | | Clotting | | Proteolytical | | Overall |
|---|---|---|---|---|---|---|---|---|---|---|
| 7 | L280I | G309D | S331Y | L224V | Y326F | 318 | | 12.257 | ++++ | + |
| 11 | L280I | G309D | H134Q | M223E | L70M | 386 | + | 10.664 | ++++ | ++ |
| 14 | L280I | G309W | L238I | T342S | | 420 | +++ | 21.087 | + | ++ |
| 17 | L280I | G309D | V213F | E320T | V90L | 426 | +++ | 21.956 | + | ++ |
| 19 | L280I | G309W | S212A | V261A | | 344 | | 10.865 | ++++ | + |
| Camel wt | | | | | | 366 | + | 15.664 | +++ | |

Statistical Analysis of the Effects of Individual Mutations

A statistical, PCA based, analysis was used to identify single mutations with positive effects on either proteolytical activity, milk clotting activity, or both. In the table below, mutations resulting in increased clotting activity, decreased proteolytical activity or both increased clotting and decreased proteolytical activity are summarized. The PCA plot is indicated in the FIG. 4.

TABLE 5 single substitutions having positive effects on clotting, proteolytical activity or on both

| Clotting + proteolytical | Clotting | Proteolytical |
|---|---|---|
| H134Q | I103V | R324V |
| L224V | F75Y | K120Q |
| Q346E | D325Q | M223E |
| L70M | I154L | S331Y |
| G309W | I361L | K379P |
| E320T | Y79S | L163E |
| L238I | D117N | |
| V90L | L280I | |
| V367I | V261A | |
| V256I | | |
| K77T | | |
| S212A | | |
| F124Y | | |

Positional Effects

It was expected that most mutations that would have an effect on clotting activity or on general proteolytical activity (i.e. specificity) would be located in or close to the catalytical cleft. The substrate is entering the catalytical cleft and it is also here that cleavage takes place.

Suprisingly, only few of the substitutions that were shown to have a positive effect on clotting activity and/or specificity were located in this region (for example L280I L70M and F75Y). Many mutations that had a positive effect were found on other parts of the molecule Substitutions Resulting in Improved Clotting Activity Most of the substitutions resulting in improved clotting activity were located in the body of the enzyme and are likely to have caused conformational changes in the molecule. Substitution F75Y is located at the entrance of the cleft and is rather subtle, resulting in increased polarity.

TABLE 6 substitutions giving improved clotting

| | |
|---|---|
| I103V | Lobe, back |
| F75Y | Cleft entrance |
| D325Q | Backbone |
| I154L | Backbone |
| I361L | Body |
| Y79S | Backbone |
| D117N | Side |
| L280I | Close to cleft |
| V261A | Side |

Substitutions Resulting in Reduced Proteolytical Activity

Most of the substitutions are located in the body of the molecule. The resulting conformational changes might result in increased accessibility for the substrate. Two mutations were found at the lobes that mark the entrance of the catalytical cleft. The L163E substitution increases the negative charge. This strengthens the results from example 7, showing the importance of charge in these positions.

TABLE 6

| Mutations resulting in reduced proteolytical activity | |
|---|---|
| R324V | Backbone |
| K120Q | Side |
| M223E | Body |
| S331Y | Lobe |
| K379P | Backbone |
| L163E | Lobe |

Substitutions Resulting in Improved Clotting and Reduced Proteolytical Activity

Some of the substitutions that result in an overall improvement of the milk clotting capabilities result in charge changes that are likely to be involved in substrate recognition. These include H134Q resulting in higher positive, as well as the Q346E substitution resulting in more negative charge. Other substitutions with positive effects on both clotting and specificity are most likely resulting in more general conformational changes of the chymosin molecule.

TABLE 7

| Mutations giving improved clotting and reduced proteolytical activity | |
|---|---|
| H134Q | Outside flap |
| L224V | Backbone |
| Q346E | Entrance cleft |
| L70M | Cleft |
| G309W | Side lobe |

TABLE 7-continued

| Mutations giving improved clotting and reduced proteolytical activity | |
|---|---|
| E320T | Backbone |
| L238I | Backbone |
| V90L | Close to cleft |
| V367I | Backbone |
| V256I | Backbone |
| K77T | Side protruding |
| S212A | Backbone |
| F124Y | Backbone |

Example 9: Evaluation of Camel Variants

Variant Characterization

Camel chymosin variants evaluated in Example 7 regarding their milk clotting (C) and general proteolytic (P) activities were produced again and evaluated regarding their casein cleavage specificity C/P (Table 1 below). The C/P ratio is a measure for a coagulant's efficiency in cheese making, i.e., the yield of cheese curd obtained from a certain volume of milk. Milk clotting and general proteolytic activities were determined as described in Examples 4 and 5, respectively. In this example, however, proteolytic activity was measured without normalization for clotting activity.

Camel chymosin was analyzed as reference. C/P values of all variants are shown as relative values to wild type camel chymosin. An impact of total protein concentration in the enzyme samples on C/P was detected, and C/P values were corrected for this correlation accordingly.

TABLE 1

Analysis of camel chymosin variants

| variant | mutations | | | | | Clotting (C) | Proteolytical (P) | C/P |
|---|---|---|---|---|---|---|---|---|
| 1 | L280I | G309D | E141S | Q220S | R324I | 92% | 125% | 25% |
| 2 | L280I | G309W | F75Y | Y79S | | 108% | 129% | 78% |
| 3 | L280I | G309D | H134Q | S222G | S331Y | 103% | 34% | 271% |
| 4 | L280I | G309D | K120Q | M223E | H239N | 96% | 81% | 85% |
| 5 | L280I | G309D | Q220S | V213F | T342S | 75% | 113% | 42% |
| 6 | L280I | G309D | H134Q | V213F | F281A | 62% | 31% | 339% |
| 7 | L280I | G309D | S331Y | L224V | Y326F | 91% | 110% | 143% |
| 8 | L280I | G309D | Y326F | V241I | E305T | 135% | 114% | 94% |
| 9 | L280I | G309D | S331Y | F124Y | I346L | 98% | 123% | 81% |
| 10 | L280I | G309D | M223E | L224V | L273V | 93% | 78% | 105% |
| 11 | L280I | G309D | H134Q | M223E | L70M | 116% | 68% | 246% |
| 12 | L280I | G309D | F75Y | S331Y | Q346E | 155% | 83% | 172% |
| 13 | L280I | G309D | L224V | I103V | L238I | 136% | 89% | 128% |
| 14 | L280I | G309W | L238I | T342S | | 124% | 159% | 89% |
| 15 | L280I | G309D | | L70M | T342S | 93% | 152% | 35% |
| 16 | L280I | G309D | Y79S | L224V | S212A | 137% | 91% | 100% |
| 17 | L280I | G309D | V213F | E320T | V90L | 133% | 163% | 46% |
| 18 | L280I | G309D | L163E | S222G | V261A | 72% | 49% | 182% |
| 19 | L280I | G309W | S212A | V261A | | 104% | 122% | 138% |
| 20 | L280I | G309D | Q220S | L224V | H134Q | 201% | 52% | 315% |
| 21 | L280I | G309W | K77T | R324I | | 160% | 102% | 139% |
| 22 | L280I | G309W | I361L | I103V | | 108% | 132% | 79% |
| 24 | L280I | G309D | Y79S | L273V | L163E | 91% | 76% | 112% |
| 25 | L280I | G309D | I154L | T235S | K379P | 112% | 118% | 112% |
| 26 | L280I | G309D | F75Y | T342S | V261A | 108% | 90% | 141% |
| 27 | L280I | G309D | V90L | K379P | V318T | 95% | 135% | 55% |
| 28 | L280I | G309D | V256I | V90L | E141S | 109% | 146% | 139% |
| 29 | L280I | G309D | I154L | V261A | V367I | 157% | 95% | 156% |
| 30 | L280I | G309D | Y326F | L273V | V90L | 99% | 119% | 58% |
| 31 | L280I | G309D | H134Q | L163E | V318T | 95% | 59% | 247% |
| 32 | L280I | G309D | Y79S | H134Q | Y326F | 105% | 66% | 219% |
| 33 | L280I | G309D | Y79S | I103V | F281A | 124% | 66% | 342% |
| 34 | L280I | G309D | V256I | V261A | K379P | 146% | 102% | 134% |
| 36 | L280I | G309D | S222G | R324V | I154L | 76% | 68% | 161% |
| 37 | L280I | G309D | H239N | F124Y | V90L | 102% | 125% | 67% |
| 38 | L280I | G309D | H239N | R324I | D325Q | 90% | 143% | 127% |
| 39 | L280I | G309W | K120Q | V367I | | 103% | 94% | 139% |
| 40 | L280I | G309D | Y326F | L70M | D325Q | 96% | 207% | 10% |

TABLE 1-continued

Analysis of camel chymosin variants

| variant | mutations | | | | Clotting (C) | Proteolytical (P) | C/P |
|---|---|---|---|---|---|---|---|
| 41 | L280I | G309D | L224V | E320T | T235S | 116% | 102% | 134% |
| 42 | L280I | G309D | S331Y | T342S | D325Q | 145% | 102% | 158% |
| 43 | L280I | G309D | F124Y | Q346E | I154L | 135% | 94% | 176% |
| 44 | L280I | G309D | V261A | R324V | F281A | 71% | 63% | 137% |
| 45 | L280I | G309D | I361L | S212A | V318T | 116% | 122% | 100% |
| 46 | L280I | G309D | Y79S | T342S | I154L | 137% | 102% | 115% |
| 47 | L280I | G309D | Q346E | K77T | T235S | 124% | 107% | 123% |
| 48 | L280I | G309D | K120Q | Y326F | K77T | 90% | 86% | 113% |
| Camel wt | | | | | | 100% | 100% | 100% |

A total of 30 out of 46 characterized variants show improved C/P compared to wild type camel chymosin (Table 2 below). A more than 3-fold improvement was observed for the three top variants 33, 6 and 20.

TABLE 2

Camel chymosin variants with improved C/P

| variant | mutations | | | | Clotting (C) | Proteolytical (P) | C/P |
|---|---|---|---|---|---|---|---|
| 33 | L280I | G309D | Y79S | I103V | F281A | 124% | 66% | 342% |
| 6 | L280I | G309D | H134Q | V213F | F281A | 62% | 31% | 339% |
| 20 | L280I | G309D | Q220S | L224V | H134Q | 201% | 52% | 315% |
| 3 | L280I | G309D | H134Q | S222G | S331Y | 103% | 34% | 271% |
| 31 | L280I | G309D | H134Q | L163E | V318T | 95% | 59% | 247% |
| 11 | L280I | G309D | H134Q | M223E | L70M | 116% | 68% | 246% |
| 32 | L280I | G309D | Y79S | H134Q | Y326F | 105% | 66% | 219% |
| 18 | L280I | G309D | L163E | S222G | V261A | 72% | 49% | 182% |
| 43 | L280I | G309D | F124Y | Q346E | I154L | 135% | 94% | 176% |
| 12 | L280I | G309D | F75Y | S331Y | Q346E | 155% | 83% | 172% |
| 36 | L280I | G309D | S222G | R324V | I154L | 76% | 68% | 161% |
| 42 | L280I | G309D | S331Y | T342S | D325Q | 145% | 102% | 158% |
| 29 | L280I | G309D | I154L | V261A | V367I | 157% | 95% | 156% |
| 7 | L280I | G309D | S331Y | L224V | Y326F | 91% | 110% | 143% |
| 26 | L280I | G309D | F75Y | T342S | V261A | 108% | 90% | 141% |
| 21 | L280I | G309W | K77T | R324I | | 160% | 102% | 139% |
| 28 | L280I | G309D | V256I | V90L | E141S | 109% | 146% | 139% |
| 39 | L280I | G309W | K120Q | V367I | | 103% | 94% | 139% |
| 19 | L280I | G309W | S212A | V261A | | 104% | 122% | 138% |
| 44 | L280I | G309D | V261A | R324V | F281A | 71% | 63% | 137% |
| 34 | L280I | G309D | V256I | V261A | K379P | 146% | 102% | 134% |
| 41 | L280I | G309D | L224V | E320T | T235S | 116% | 102% | 134% |
| 13 | L280I | G309D | L224V | I103V | L238I | 136% | 89% | 128% |
| 38 | L280I | G309D | H239N | R324I | D325Q | 90% | 143% | 127% |
| 47 | L280I | G309D | Q346E | K77T | T235S | 124% | 107% | 123% |
| 46 | L280I | G309D | Y79S | T342S | I154L | 137% | 102% | 115% |
| 48 | L280I | G309D | K120Q | Y326F | K77T | 90% | 86% | 113% |
| 24 | L280I | G309D | Y79S | L273V | L163E | 91% | 76% | 112% |
| 25 | L280I | G309D | I154L | T235S | K379P | 112% | 118% | 112% |
| 10 | L280I | G309D | M223E | L224V | L273V | 93% | 78% | 105% |
| Camel wt | | | | | | 100% | 100% | 100% |

Statistical Analysis of the Positional and Mutational Effects on C/P

A statistical, PCA based, analysis was used to identify single mutations with positive effects on the specificity of milk clotting over general casein proteolysis (C/P) of camel chymosin. The following mutations were found to be beneficial for high C/P ratios:
H134Q, F281A, I103V, V256I, I154L, S222G, L224V, Q346E, S331Y, K77T, V367I, G309D, V261A, D325Q, L280I, D117N, L163E, S212A Example 10: Evaluation of Camel Variants Variant Characterization Based on the positional and mutational effects determined in Example 7, another set of camel chymosin variants was generated with multiple substitutions as compared to wild type camel chymosin and evaluated regarding their casein substrate specificity (C/P) as described in Example 9 (Table 1 below).

TABLE 1

Analysis of camel chymosin variants

| variant | mutations | | | | | | | | Clotting (C) | Proteolytical (P) | C/P |
|---|---|---|---|---|---|---|---|---|---|---|---|
| 1 | L70M | Y79S | D117N | H134Q | M223E | V256I | L280I | G309D | Q346E | 132% | 116% | 117% |
| 2 | L70M | Y79S | D117N | H134Q | M223E | L280I | G309W | S331Y | | 131% | 56% | 194% |

TABLE 1-continued

Analysis of camel chymosin variants

| variant | mutations | | | | | | | | | Clotting (C) | Proteolytical (P) | C/P |
|---|---|---|---|---|---|---|---|---|---|---|---|---|
| 3 | L70M | D117N | H134Q | M223E | V256I | L280I | G309D | S331Y | K379P | 109% | 75% | 135% |
| 4 | L70M | D117N | H134Q | S212A | M223E | V261A | L280I | G309D | V367I | 83% | 115% | 108% |
| 5 | L70M | D117N | H134Q | D156V | L280I | | | | | 135% | 108% | 137% |
| 6 | L70M | K77T | V90L | D117N | H134Q | D202Q | M223E | L280I | G309D | 135% | 113% | 124% |
| 7 | L70M | Y79S | D117N | H134Q | M223E | V261A | L280I | G309D | E320T | 141% | 124% | 143% |
| 8 | L70M | V109L | H134Q | M223E | G309D | | | | | 82% | 86% | 87% |
| 9 | L70M | D117N | F124Y | H134Q | M223E | L238I | L280I | G309D | V367I | 105% | 97% | 115% |
| 10 | L70M | D117N | H134Q | S212A | M223E | L280I | G309W | Q346E | | 101% | 79% | 133% |
| 11 | L70M | D117N | H134Q | D156V | M223E | L280I | G309D | E320T | Q346E | 153% | 101% | 119% |
| 12 | L70M | V109L | D117N | H134Q | L224V | L280I | G309D | | | 98% | 71% | 128% |
| 13 | L70M | D117N | H134Q | D202Q | M223E | V261A | L280I | | | 116% | 144% | 126% |
| 14 | L70M | D117N | D202Q | M223E | L224V | L280I | G309D | | | 85% | 126% | 111% |
| 15 | L70M | K77T | D117N | H134Q | S212A | M223E | V256I | L280I | G309D | 154% | 130% | 129% |
| 16 | L70M | H134Q | D156V | M223E | L280I | G309W | | | | 136% | 131% | 137% |
| 17 | L70M | V90L | D117N | H134Q | M223E | L238I | V256I | L280I | G309D | 121% | 101% | 97% |
| 18 | L70M | D117N | H134Q | S212A | M223E | S331Y | | | | 124% | 76% | 151% |
| 19 | L70M | V109L | D117N | F124Y | H134Q | M223E | V261A | L280I | G309W | 96% | 98% | 128% |
| 20 | L70M | V90L | H134Q | M223E | L280I | E320T | | | | 138% | 110% | 98% |
| 21 | L70M | N108D | D117N | H134Q | M223E | G309W | E320T | | | 187% | 151% | 138% |
| 22 | V109L | D117N | H134Q | M223E | L238I | L280I | G309D | E320T | | 110% | 93% | 106% |
| 23 | L70M | D117N | H134Q | M223E | G309D | Q346E | V367I | K379P | | 67% | 102% | 118% |
| 24 | L70M | N108D | D117N | V261A | L280I | G309D | | | | 95% | 117% | 102% |
| 25 | L70M | D117N | H134Q | L238I | L280I | G309W | K379P | | | 97% | 92% | 113% |
| 26 | L70M | Y79S | D117N | M223E | L280I | K379P | | | | 137% | 123% | 129% |
| 27 | D117N | H134Q | M223E | L224V | V256I | L280I | | | | 132% | 102% | 127% |
| 28 | L70M | K77T | N108D | D117N | H134Q | M223E | L280I | Q346E | | 167% | 106% | 166% |
| 29 | L70M | Y79S | N108D | D117N | F124Y | H134Q | D202Q | M223E | L280I | G309D | 183% | 57% | 151% |
| Bovine wt | | | | | | | | | | 100% | 100% | 100% |

A total of 26 out of 29 variants show improved C/P ratios, as compared to wild type camel chymosin. A 2-fold improvement was observed for the best variant (Table 2, below).

TABLE 2

Camel chymosin variants with improved C/P

| variant | mutations | | | | | | | | | Clotting (C) | Proteolytical (P) | C/P |
|---|---|---|---|---|---|---|---|---|---|---|---|---|
| 2 | L70M | Y79S | D117N | H134Q | M223E | L280I | G309W | S331Y | | 131% | 56% | 194% |
| 28 | L70M | K77T | N108D | D117N | H134Q | M223E | L280I | Q346E | | 167% | 106% | 166% |
| 18 | L70M | D117N | H134Q | S212A | M223E | S331Y | | | | 124% | 76% | 151% |
| 29 | L70M | Y79S | N108D | D117N | F124Y | H134Q | D202Q | M223E | L280I | G309D | 183% | 57% | 151% |
| 7 | L70M | Y79S | D117N | H134Q | M223E | V261A | L280I | G309D | E320T | 141% | 124% | 143% |
| 21 | L70M | N108D | D117N | H134Q | M223E | G309W | E320T | | | 187% | 151% | 138% |
| 5 | L70M | D117N | H134Q | D156V | L280I | | | | | 135% | 108% | 137% |
| 16 | L70M | H134Q | D156V | M223E | L280I | G309W | | | | 136% | 131% | 137% |
| 3 | L70M | D117N | H134Q | M223E | V256I | L280I | G309D | S331Y | K379P | 109% | 75% | 135% |
| 10 | L70M | D117N | H134Q | S212A | M223E | L280I | G309W | Q346E | | 101% | 79% | 133% |
| 15 | L70M | K77T | D117N | H134Q | S212A | M223E | V256I | L280I | G309D | 154% | 130% | 129% |
| 26 | L70M | Y79S | D117N | M223E | L280I | K379P | | | | 137% | 123% | 129% |
| 12 | L70M | V109L | D117N | H134Q | L224V | L280I | G309D | | | 98% | 71% | 128% |
| 19 | L70M | V109L | D117N | F124Y | H134Q | M223E | V261A | L280I | G309W | 96% | 98% | 128% |
| 27 | D117N | H134Q | M223E | L224V | V256I | L280I | | | | 132% | 102% | 127% |
| 13 | L70M | D117N | H134Q | D202Q | M223E | V261A | L280I | | | 116% | 144% | 126% |
| 6 | L70M | K77T | V90L | D117N | H134Q | D202Q | M223E | L280I | G309D | 135% | 113% | 124% |
| 11 | L70M | D117N | H134Q | D156V | M223E | L280I | G309D | E320T | Q346E | 153% | 101% | 119% |
| 23 | L70M | D117N | H134Q | M223E | G309D | Q346E | V367I | K379P | | 67% | 102% | 118% |
| 1 | L70M | Y79S | D117N | H134Q | M223E | V256I | L280I | G309D | Q346E | 132% | 116% | 117% |
| 9 | L70M | D117N | F124Y | H134Q | M223E | L238I | L280I | G309D | V367I | 105% | 97% | 115% |
| 25 | L70M | D117N | H134Q | L238I | L280I | G309W | K379P | | | 97% | 92% | 113% |
| 14 | L70M | D117N | D202Q | M223E | L224V | L280I | G309D | | | 85% | 126% | 111% |
| 4 | L70M | D117N | H134Q | S212A | M223E | V261A | L280I | G309D | V367I | 83% | 115% | 108% |
| 22 | V109L | D117N | H134Q | M223E | L238I | L280I | G309D | E320T | | 110% | 93% | 106% |
| 24 | L70M | N108D | D117N | V261A | L280I | G309D | | | | 95% | 117% | 102% |
| Camel wt | | | | | | | | | | 100% | 100% | 100% |

Statistical Analysis of the Positional and Mutational Effects on C/P

A statistical, PCA based, analysis was used to identify single mutations with positive effects on the specificity of milk clotting over general casein proteolysis (C/P) of camel chymosin. The following mutations were found to be beneficial for high C/P ratios:

S331Y, Y79S, K77T, D117N, H134Q, N108D, G309W, L224V, D156V, L280I, M223E, V367I, F114Y

Example 11: Evaluation of Camel Variants

A statistical, PCA based, analysis was performed on the combined set of variants from Examples 9 and 10, and single mutations were identified with positive effects on the specificity of milk clotting over general casein proteolysis (C/P) of camel chymosin. The following mutations were found to be beneficial for high C/P ratios:
F281A, H134Q, I103V, S331Y, S222G, I154L, L280I, G309D, D117N, L224V, N108D, L163E, G309W, K77T, Y79S These mutations agree well with the beneficial mutations determined in Examples 9 and 10.
Structural Evaluation of Positional and Mutational Effects on C/P As seen in Example 8, the majority of beneficial mutations are again located distant from the substrate binding cleft. Only L280I and F281A are located directly in the cleft (Gilliland et al. 1990). I280 points into the hydrophobic core of the C-terminal lobe. This mutation might therefore lead to subtle conformational changes of the binding cleft and, thus, influence substrate specificity. Position 281 is part of the S2 binding site and interacts with the P2 position in the casein substrate. A mutation in this position is very likely to have an impact on casein binding and, thus, proteolysis. Mutations G309W and S331Y are positioned on the surface of the C-terminal lobe in a region that has been described to interact with K-casein to aid substrate binding in the catalytic cleft (Gilliland et al. 1990). These mutations might therefore have a positive impact on substrate binding. I154L and D156V, and L163E represent changes to the core of the N-terminal lobe, possibly leading to subtle structural rearrangements of the enzyme with impact on catalytic activity. Mutations S222G and L224V introduce changes into the beta sheet that might interact with the protein N-terminus in its activated form (Langholm Jensen et al.). Potential effects on the activation state of the enzyme could result in shifted casein substrate specificity. The remaining hit mutations K77T, Y79S, I103V, N108D, D117N, and H134Q are located on the surface of the N-terminal lobe and, with exception of I103V, represent exchanges of polar amino acids. These changes on the surface of the enzyme most probably influence interactions with casein molecules leading to improved specificity in favor of κ-casein.

REFERENCES

1: WO02/36752A2 (Chr. Hansen)
2: Suzuki et al: Site directed mutagenesis reveals functional contribution of Thr218, Lys220 and Asp304 in chymosin, Protein Engineering, vol. 4, January 1990, pages 69-71
3: Suzuki et al: Alteration of catalytic properties of chymosin by site-directed mutagenesis, Protein Engineering, vol. 2, May 1989, pages 563-569
4: van den Brink et al: Increased production of chymosin by glycosylation, Journal of biotechnology, vol. 125, September 2006, pages 304-310.
5: Pitts et al: Expression and characterisation of chymosin pH optima mutants produced in *Tricoderma reesei*, Journal of biotechnology, vol. 28, March 1993, pages 69-83
6: M. G. Williams et al: Mutagenesis, biochemical characterization and X-ray structural analysis of point mutants of bovine chymosin, Protein engineering design and selection, vol. 10, September 1997, pages 991-997
7: Strop et al: Engineering enzyme subsite specificity: preparation, kinetic characterization, and x-ray analysis at 2.0 ANG resolution of Val111phe site mutated calf chymosin, Biochemistry, vol. 29, October 1990, pages 9863-9871
8: Supannee et al: Site-specific mutations of calf chymosin B which influence milk-clotting activity, Food Chemistry, vol. 62, June 1998, pages 133-139
9: Zhang et al: Functional implications of disulfide bond, Cys45-Cys50, in recombinant prochymosin, Biochimica et biophysica acta, vol. 1343, December 1997, pages 278-286.
10: WO2013/174840A1 (Chr. Hansen).
11: WO2013/164479A2 (DSM).
12: Langholm Jensen et al: Camel and bovine chymosin: the relationship between their structures and cheese-making properties, Acta Crystallographica Section D: Biological Crystallography, vol. 69, 2013, pages 901-913.
13: Gilliland et al: The three-dimensional structure of bovine chymosin at 2.3 Å resolution, Proteins, vol. 8, 1990, pages 82-101.

---

The invention claimed is:

1. A method for making an isolated chymosin polypeptide variant comprising:
   (a) producing and isolating a chymosin polypeptide variant of a parent polypeptide having chymosin activity, wherein the amino acid sequence of the variant differs from the amino acid sequence of the parent by having an alteration comprising a substitution at at least one amino acid position of the parent sequence corresponding to any of positions 77, 154, 212, 224, 246, and 367, wherein the corresponding position in the parent sequence is determined by alignment of the parent sequence with SEQ ID NO:1 (bovine chymosin), thereby obtaining the isolated chymosin polypeptide variant, wherein the variant has chymosin activity; wherein:

the amino acid sequence of the parent polypeptide has at least 65% sequence identity with the amino acid sequence from position 59 to position 381 of SEQ ID NO: 1 (the mature bovine chymosin polypeptide); and the variant has fewer than 30 amino acid alterations in the region from amino acid position 59 to amino acid position 381 as compared to the mature polypeptide from amino acid position 59 to amino acid position 381 of SEQ ID NO:1 or as compared to the mature polypeptide from amino acid position 59 to amino acid position 381 of SEQ ID NO:2, as determined by an alignment of the amino acid sequence of the variant with the amino acid sequence of SEQ ID NO:1 or SEQ ID NO:2, respectively;

with the proviso that the isolated chymosin polypeptide variant is NOT a specific variant having any of the following sets of substitutions based on the numbering of SEQ ID NO:1:
Q246E+G309D+S329P+D337E;
R125Q+G128N+H204R+Q246E+S284T;
Y185F+R213Q+Q246E;
D216S+L224V+V263I+F281V+G309D;
Y79S+L224V+L311I; and
R119S+L224V+T297S.

2. The method for making an isolated chymosin polypeptide variant of claim 1, wherein the isolated chymosin polypeptide variant has:
  (i) a chymosin activity giving a higher clotting activity to proteolytical activity (C/P) ratio as compared to the C/P ratio of bovine chymosin comprising the amino acid sequence from position 59 to position 381 of SEQ ID NO:1; and
  (ii) a chymosin activity giving a higher C/P ratio as compared to the C/P ratio of camel chymosin comprising the amino acid sequence from amino acid position 59 to amino acid position 381 of SEQ ID NO:2.

3. The method for making an isolated chymosin polypeptide variant of claim 1, wherein the alteration comprises at least one substitution selected from K77T; I154L; S212A; L224V; Q246E; and V367I.

4. The method for making an isolated chymosin polypeptide variant of claim 3, wherein the alteration comprises Q246E.

5. The method for making an isolated chymosin polypeptide variant of claim 1, wherein the alteration comprises substitutions selected from:
H134Q+Q246E+Y326F;
D156V+Q246E+L280I;
L280I+G309D+L224V+E320T+T235S;
L280I+G309W+K77T+R324I;
L280I+G309D+Q220S+L224V+H134Q;
L280I+G309D+L224V+I103V+L238I;
L280I+G309D+F124Y+Q346E+I154L;
L280I+G309D+I154L+V261A+V367I;
L280I+G309D+Y79S+L224V+S212A;
L280I+G309D+Y79S+T342S+I154L;
L280I+G309D+Q346E+K77T+T235S;
L280I+G309D+S331Y+L224V+Y326F;
L280I+G309D+Y79S+L224V+S212A;
L280I+G309D+S331Y+L224V+Y326F; and
L280I+G309W+S212A+V261A.

6. The method for making an isolated chymosin polypeptide variant of claim 1, wherein the amino acid sequence of the parent polypeptide has at least 95% sequence identity with the amino acid sequence from position 59 to position 381 of SEQ ID NO:1.

7. The method for making an isolated chymosin polypeptide variant of claim 1, wherein the amino acid sequence of the parent polypeptide has at least 95% sequence identity with the amino acid sequence from position 59 to position 381 of SEQ ID NO:2.

* * * * *

SEQUENCE LISTING

```
<160> NUMBER OF SEQ ID NOS: 10

<210> SEQ ID NO 1
<211> LENGTH: 381
<212> TYPE: PRT
<213> ORGANISM: Bos taurus

<400> SEQUENCE: 1

Met Arg Cys Leu Val Val Leu Leu Ala Val Phe Ala Leu Ser Gln Gly
1               5                   10                  15

Ala Glu Ile Thr Arg Ile Pro Leu Tyr Lys Gly Lys Ser Leu Arg Lys
            20                  25                  30

Ala Leu Lys Glu His Gly Leu Leu Glu Asp Phe Leu Gln Lys Gln Gln
        35                  40                  45

Tyr Gly Ile Ser Ser Lys Tyr Ser Gly Phe Gly Glu Val Ala Ser Val
    50                  55                  60

Pro Leu Thr Asn Tyr Leu Asp Ser Gln Tyr Phe Gly Lys Ile Tyr Leu
65                  70                  75                  80
```

Gly Thr Pro Pro Gln Glu Phe Thr Val Leu Phe Asp Thr Gly Ser Ser
                85                  90                  95

Asp Phe Trp Val Pro Ser Ile Tyr Cys Lys Ser Asn Ala Cys Lys Asn
            100                 105                 110

His Gln Arg Phe Asp Pro Arg Lys Ser Ser Thr Phe Gln Asn Leu Gly
        115                 120                 125

Lys Pro Leu Ser Ile His Tyr Gly Thr Gly Ser Met Gln Gly Ile Leu
    130                 135                 140

Gly Tyr Asp Thr Val Thr Val Ser Asn Ile Val Asp Ile Gln Gln Thr
145                 150                 155                 160

Val Gly Leu Ser Thr Gln Glu Pro Gly Asp Val Phe Thr Tyr Ala Glu
                165                 170                 175

Phe Asp Gly Ile Leu Gly Met Ala Tyr Pro Ser Leu Ala Ser Glu Tyr
            180                 185                 190

Ser Ile Pro Val Phe Asp Asn Met Met Asn Arg His Leu Val Ala Gln
        195                 200                 205

Asp Leu Phe Ser Val Tyr Met Asp Arg Asn Gly Gln Glu Ser Met Leu
    210                 215                 220

Thr Leu Gly Ala Ile Asp Pro Ser Tyr Tyr Thr Gly Ser Leu His Trp
225                 230                 235                 240

Val Pro Val Thr Val Gln Gln Tyr Trp Gln Phe Thr Val Asp Ser Val
                245                 250                 255

Thr Ile Ser Gly Val Val Ala Cys Glu Gly Gly Cys Gln Ala Ile
            260                 265                 270

Leu Asp Thr Gly Thr Ser Lys Leu Val Gly Pro Ser Ser Asp Ile Leu
    275                 280                 285

Asn Ile Gln Gln Ala Ile Gly Ala Thr Gln Asn Gln Tyr Gly Glu Phe
290                 295                 300

Asp Ile Asp Cys Asp Asn Leu Ser Tyr Met Pro Thr Val Val Phe Glu
305                 310                 315                 320

Ile Asn Gly Lys Met Tyr Pro Leu Thr Pro Ser Ala Tyr Thr Ser Gln
                325                 330                 335

Asp Gln Gly Phe Cys Thr Ser Gly Phe Gln Ser Glu Asn His Ser Gln
            340                 345                 350

Lys Trp Ile Leu Gly Asp Val Phe Ile Arg Glu Tyr Tyr Ser Val Phe
        355                 360                 365

Asp Arg Ala Asn Asn Leu Val Gly Leu Ala Lys Ala Ile
    370                 375                 380

<210> SEQ ID NO 2
<211> LENGTH: 381
<212> TYPE: PRT
<213> ORGANISM: Camelus dromedarius

<400> SEQUENCE: 2

Met Arg Cys Leu Val Val Leu Leu Ala Ala Leu Ala Leu Ser Gln Ala
1               5                   10                  15

Ser Gly Ile Thr Arg Ile Pro Leu His Lys Gly Lys Thr Leu Arg Lys
                20                  25                  30

Ala Leu Lys Glu Arg Gly Leu Leu Glu Asp Phe Leu Gln Arg Gln Gln
            35                  40                  45

Tyr Ala Val Ser Ser Lys Tyr Ser Ser Leu Gly Lys Val Ala Arg Glu
        50                  55                  60

Pro Leu Thr Ser Tyr Leu Asp Ser Gln Tyr Phe Gly Lys Ile Tyr Ile
65                  70                  75                  80

-continued

```
Gly Thr Pro Pro Gln Glu Phe Thr Val Val Phe Asp Thr Gly Ser Ser
                 85                  90                  95

Asp Leu Trp Val Pro Ser Ile Tyr Cys Lys Ser Asn Val Cys Lys Asn
            100                 105                 110

His His Arg Phe Asp Pro Arg Lys Ser Ser Thr Phe Arg Asn Leu Gly
        115                 120                 125

Lys Pro Leu Ser Ile His Tyr Gly Thr Gly Ser Met Glu Gly Phe Leu
    130                 135                 140

Gly Tyr Asp Thr Val Thr Val Ser Asn Ile Val Asp Pro Asn Gln Thr
145                 150                 155                 160

Val Gly Leu Ser Thr Glu Gln Pro Gly Glu Val Phe Thr Tyr Ser Glu
                165                 170                 175

Phe Asp Gly Ile Leu Gly Leu Ala Tyr Pro Ser Leu Ala Ser Glu Tyr
            180                 185                 190

Ser Val Pro Val Phe Asp Asn Met Met Asp Arg His Leu Val Ala Arg
        195                 200                 205

Asp Leu Phe Ser Val Tyr Met Asp Arg Asn Gly Gln Gly Ser Met Leu
    210                 215                 220

Thr Leu Gly Ala Ile Asp Pro Ser Tyr Tyr Thr Gly Ser Leu His Trp
225                 230                 235                 240

Val Pro Val Thr Leu Gln Gln Tyr Trp Gln Phe Thr Val Asp Ser Val
                245                 250                 255

Thr Ile Asn Gly Val Ala Val Ala Cys Val Gly Gly Cys Gln Ala Ile
            260                 265                 270

Leu Asp Thr Gly Thr Ser Val Leu Phe Gly Pro Ser Ser Asp Ile Leu
        275                 280                 285

Lys Ile Gln Met Ala Ile Gly Ala Thr Glu Asn Arg Tyr Gly Glu Phe
    290                 295                 300

Asp Val Asn Cys Gly Asn Leu Arg Ser Met Pro Thr Val Val Phe Glu
305                 310                 315                 320

Ile Asn Gly Arg Asp Tyr Pro Leu Ser Pro Ser Ala Tyr Thr Ser Lys
                325                 330                 335

Asp Gln Gly Phe Cys Thr Ser Gly Phe Gln Gly Asp Asn Asn Ser Glu
            340                 345                 350

Leu Trp Ile Leu Gly Asp Val Phe Ile Arg Glu Tyr Tyr Ser Val Phe
        355                 360                 365

Asp Arg Ala Asn Asn Arg Val Gly Leu Ala Lys Ala Ile
    370                 375                 380

<210> SEQ ID NO 3
<211> LENGTH: 381
<212> TYPE: PRT
<213> ORGANISM: Ovis aries

<400> SEQUENCE: 3

Met Arg Cys Leu Val Val Leu Leu Ala Val Phe Ala Leu Ser Gln Gly
1               5                   10                  15

Ala Glu Ile Thr Arg Ile Pro Leu Tyr Lys Gly Lys Pro Leu Arg Lys
            20                  25                  30

Ala Leu Lys Glu Arg Gly Leu Leu Glu Asp Phe Leu Gln Lys Gln Gln
        35                  40                  45

Tyr Gly Val Ser Ser Glu Tyr Ser Gly Phe Gly Glu Val Ala Ser Val
    50                  55                  60

Pro Leu Thr Asn Tyr Leu Asp Ser Gln Tyr Phe Gly Lys Ile Tyr Leu
65                  70                  75                  80
```

Gly Thr Pro Pro Gln Glu Phe Thr Val Leu Phe Asp Thr Gly Ser Ser
                 85                  90                  95

Asp Phe Trp Val Pro Ser Ile Tyr Cys Lys Ser Asn Ala Cys Lys Asn
            100                 105                 110

His Gln Arg Phe Asp Pro Arg Lys Ser Ser Thr Phe Gln Asn Leu Gly
        115                 120                 125

Lys Pro Leu Ser Ile Arg Tyr Gly Thr Gly Ser Met Gln Gly Ile Leu
130                 135                 140

Gly Tyr Asp Thr Val Thr Val Ser Asn Ile Val Asp Ile Gln Gln Thr
145                 150                 155                 160

Val Gly Leu Ser Thr Gln Glu Pro Gly Asp Val Phe Thr Tyr Ala Glu
                165                 170                 175

Phe Asp Gly Ile Leu Gly Met Ala Tyr Pro Ser Leu Ala Ser Glu Tyr
            180                 185                 190

Ser Val Pro Val Phe Asp Asn Met Met Asp Arg Arg Leu Val Ala Gln
        195                 200                 205

Asp Leu Phe Ser Val Tyr Met Asp Arg Ser Gly Gln Gly Ser Met Leu
210                 215                 220

Thr Leu Gly Ala Ile Asp Pro Ser Tyr Tyr Thr Gly Ser Leu His Trp
225                 230                 235                 240

Val Pro Val Thr Leu Gln Lys Tyr Trp Gln Phe Thr Val Asp Ser Val
                245                 250                 255

Thr Ile Ser Gly Ala Val Val Ala Cys Glu Gly Gly Cys Gln Ala Ile
            260                 265                 270

Leu Asp Thr Gly Thr Ser Lys Leu Val Gly Pro Ser Ser Asp Ile Leu
        275                 280                 285

Asn Ile Gln Gln Ala Ile Gly Ala Thr Gln Asn Gln Tyr Gly Glu Phe
290                 295                 300

Asp Ile Asp Cys Asp Ser Leu Ser Ser Met Pro Thr Val Val Phe Glu
305                 310                 315                 320

Ile Asn Gly Lys Met Tyr Pro Leu Thr Pro Tyr Ala Tyr Thr Ser Gln
                325                 330                 335

Glu Glu Gly Phe Cys Thr Ser Gly Phe Gln Gly Glu Asn His Ser His
            340                 345                 350

Gln Trp Ile Leu Gly Asp Val Phe Ile Arg Glu Tyr Tyr Ser Val Phe
        355                 360                 365

Asp Arg Ala Asn Asn Leu Val Gly Leu Ala Lys Ala Ile
370                 375                 380

<210> SEQ ID NO 4
<211> LENGTH: 381
<212> TYPE: PRT
<213> ORGANISM: Camelus bactrianus

<400> SEQUENCE: 4

Met Arg Cys Leu Val Val Leu Leu Ala Ala Leu Ala Leu Ser Gln Ala
1               5                   10                  15

Ser Gly Ile Thr Arg Ile Pro Leu His Lys Gly Lys Thr Leu Arg Lys
            20                  25                  30

Ala Leu Lys Glu Arg Gly Leu Leu Glu Asp Phe Leu Gln Arg Gln Gln
        35                  40                  45

Tyr Ala Val Ser Ser Lys Tyr Ser Ser Leu Gly Lys Val Ala Arg Glu
    50                  55                  60

Pro Leu Thr Ser Tyr Leu Asp Ser Gln Tyr Phe Gly Lys Ile Tyr Ile
65                  70                  75                  80

Gly Thr Pro Pro Gln Glu Phe Thr Val Val Phe Asp Thr Gly Ser Ser
            85                  90                  95

Asp Leu Trp Val Pro Ser Ile Tyr Cys Lys Ser Asn Ala Cys Lys Asn
        100                 105                 110

His His Arg Phe Asp Pro Arg Lys Ser Ser Thr Phe Arg Asn Leu Gly
            115                 120                 125

Lys Pro Leu Ser Ile His Tyr Gly Thr Gly Ser Ile Glu Gly Phe Leu
130                 135                 140

Gly Tyr Asp Thr Val Thr Val Ser Asn Ile Val Asp Pro Asn Gln Thr
145                 150                 155                 160

Val Gly Leu Ser Thr Glu Gln Pro Gly Glu Val Phe Thr Tyr Ser Glu
                165                 170                 175

Phe Asp Gly Ile Leu Gly Leu Ala Tyr Pro Ser Leu Ala Ser Glu Tyr
            180                 185                 190

Ser Val Pro Val Phe Asp Asn Met Met Asp Arg His Leu Val Ala Arg
        195                 200                 205

Asp Leu Phe Ser Val Tyr Met Asp Arg Asn Gly Gln Gly Ser Met Leu
    210                 215                 220

Thr Leu Gly Ala Thr Asp Pro Ser Tyr Tyr Thr Gly Ser Leu His Trp
225                 230                 235                 240

Val Pro Val Thr Val Gln Gln Tyr Trp Gln Val Thr Val Asp Ser Val
                245                 250                 255

Thr Ile Asn Gly Val Ala Val Ala Cys Val Gly Gly Cys Gln Ala Ile
            260                 265                 270

Leu Asp Thr Gly Thr Ser Val Leu Phe Gly Pro Ser Ser Asp Ile Leu
        275                 280                 285

Lys Ile Gln Met Ala Ile Gly Ala Thr Glu Asn Arg Tyr Gly Glu Phe
290                 295                 300

Asp Val Asn Cys Gly Ser Leu Arg Ser Met Pro Thr Val Val Phe Glu
305                 310                 315                 320

Ile Asn Gly Arg Asp Phe Pro Leu Ala Pro Ser Ala Tyr Thr Ser Lys
                325                 330                 335

Asp Gln Gly Phe Cys Thr Ser Gly Phe Gln Gly Asp Asn Asn Ser Glu
            340                 345                 350

Leu Trp Ile Leu Gly Asp Val Phe Ile Arg Glu Tyr Tyr Ser Val Phe
        355                 360                 365

Asp Arg Ala Asn Asn Arg Val Gly Leu Ala Lys Ala Ile
    370                 375                 380

<210> SEQ ID NO 5
<211> LENGTH: 380
<212> TYPE: PRT
<213> ORGANISM: Sus scrofa

<400> SEQUENCE: 5

Ile Arg Gly Arg Val Leu Leu Ala Val Leu Ala Leu Ser Gln Gly Ser
1               5                   10                  15

Gly Ile Thr Arg Val Pro Leu Arg Lys Gly Lys Ser Leu Arg Lys Glu
            20                  25                  30

Leu Lys Glu Arg Gly Leu Leu Glu Asp Phe Leu Gln Lys Gln Pro Tyr
        35                  40                  45

Ala Leu Ser Ser Lys Tyr Ser Ser Phe Gly Glu Val Ala Ser Glu Pro
    50                  55                  60

Leu Thr Asn Tyr Leu Asp Thr Gln Tyr Phe Gly Lys Ile Tyr Ile Gly
65                  70                  75                  80

```
Thr Pro Pro Gln Glu Phe Thr Val Val Phe Asp Thr Gly Ser Ser Glu
                85                  90                  95

Leu Trp Val Pro Ser Val Tyr Cys Lys Ser Asp Ala Cys Gln Asn His
            100                 105                 110

His Arg Phe Asn Pro Ser Lys Ser Ser Thr Phe Gln Asn Leu Asp Lys
        115                 120                 125

Pro Leu Ser Ile Gln Tyr Gly Thr Gly Ser Ile Gln Gly Phe Leu Gly
    130                 135                 140

Tyr Asp Thr Val Met Val Ala Gly Ile Val Asp Ala His Gln Thr Val
145                 150                 155                 160

Gly Leu Ser Thr Gln Glu Pro Ser Asp Ile Phe Thr Tyr Ser Glu Phe
                165                 170                 175

Asp Gly Ile Leu Gly Leu Gly Tyr Pro Glu Leu Ala Ser Glu Tyr Thr
            180                 185                 190

Val Pro Val Phe Asp Asn Met Met His Arg His Leu Val Ala Gln Asp
        195                 200                 205

Leu Phe Ala Val Tyr Met Ser Arg Asn Asp Glu Gly Ser Met Leu Thr
    210                 215                 220

Leu Gly Ala Ile Asp Pro Ser Tyr Tyr Thr Gly Ser Leu His Trp Val
225                 230                 235                 240

Pro Val Thr Met Gln Leu Tyr Trp Gln Phe Thr Val Asp Ser Val Thr
                245                 250                 255

Ile Asn Gly Val Val Ala Cys Asn Gly Gly Cys Gln Ala Ile Leu
            260                 265                 270

Asp Thr Gly Thr Ser Met Leu Ala Gly Pro Ser Ser Asp Ile Leu Asn
        275                 280                 285

Ile Gln Met Ala Ile Gly Ala Thr Glu Ser Gln Tyr Gly Glu Phe Asp
    290                 295                 300

Ile Asp Cys Gly Ser Leu Ser Ser Met Pro Thr Val Val Phe Glu Ile
305                 310                 315                 320

Ser Gly Arg Met Tyr Pro Leu Pro Pro Ser Ala Tyr Thr Asn Gln Asp
                325                 330                 335

Gln Gly Phe Cys Thr Ser Gly Phe Gln Gly Asp Ser Lys Ser Gln His
            340                 345                 350

Trp Ile Leu Gly Val Val Phe Ile Gln Glu Tyr Tyr Ser Val Phe Asp
    355                 360                 365

Arg Ala Asn Asn Arg Val Gly Leu Ala Lys Ala Ile
370                 375                 380

<210> SEQ ID NO 6
<211> LENGTH: 379
<212> TYPE: PRT
<213> ORGANISM: Rattus norvegicus

<400> SEQUENCE: 6

Met Arg Cys Phe Val Leu Leu Leu Ala Val Leu Ala Ile Ala Gln Ser
1               5                   10                  15

His Val Val Thr Arg Ile Pro Leu His Lys Gly Lys Ser Leu Arg Asn
                20                  25                  30

Thr Leu Lys Glu Gln Gly Leu Leu Glu Asp Phe Leu Arg Arg His Gln
            35                  40                  45

Tyr Glu Phe Ser Glu Lys Asn Ser Asn Ile Gly Met Val Ala Ser Glu
    50                  55                  60

Pro Leu Thr Asn Tyr Leu Asp Ser Glu Tyr Phe Gly Leu Ile Tyr Val
65                  70                  75                  80
```

```
Gly Thr Pro Pro Gln Glu Phe Lys Val Val Phe Asp Thr Gly Ser Ser
                    85                  90                  95

Glu Leu Trp Val Pro Ser Val Tyr Cys Ser Ser Lys Val Cys Arg Asn
            100                 105                 110

His Asn Arg Phe Asp Pro Ser Lys Ser Phe Thr Phe Gln Asn Leu Ser
        115                 120                 125

Lys Pro Leu Phe Val Gln Tyr Gly Thr Gly Ser Val Glu Gly Phe Leu
    130                 135                 140

Ala Tyr Asp Thr Val Thr Val Ser Asp Ile Val Pro His Gln Thr
145                 150                 155                 160

Val Gly Leu Ser Thr Glu Glu Pro Gly Asp Ile Phe Thr Tyr Ser Pro
                    165                 170                 175

Phe Asp Gly Ile Leu Gly Leu Ala Tyr Pro Thr Phe Ala Ser Lys Tyr
                180                 185                 190

Ser Val Pro Ile Phe Asp Asn Met Met Asn Arg His Leu Val Ala Gln
                195                 200                 205

Asp Leu Phe Ser Val Tyr Met Ser Arg Asn Asp Gln Gly Ser Met Leu
        210                 215                 220

Thr Leu Gly Ala Ile Asp Gln Ser Tyr Phe Ile Gly Ser Leu His Trp
225                 230                 235                 240

Val Pro Val Thr Val Gln Gly Tyr Trp Gln Phe Thr Val Asp Arg Ile
                245                 250                 255

Thr Ile Asn Asp Glu Val Val Ala Cys Gln Gly Gly Cys Pro Ala Val
                260                 265                 270

Leu Asp Thr Gly Thr Ala Leu Leu Thr Gly Pro Gly Arg Asp Ile Leu
            275                 280                 285

Asn Ile Gln His Ala Ile Gly Ala Val Gln Gly Gln His Asp Gln Phe
    290                 295                 300

Asp Ile Asp Cys Trp Arg Leu Asn Phe Met Pro Thr Val Val Phe Glu
305                 310                 315                 320

Ile Asn Gly Arg Glu Phe Pro Leu Pro Pro Ser Ala Tyr Thr Asn Gln
                325                 330                 335

Phe Gln Gly Ser Cys Ser Ser Gly Phe Arg His Gly Ser Gln Met Trp
            340                 345                 350

Ile Leu Gly Asp Val Phe Ile Arg Glu Phe Tyr Ser Val Phe Asp Arg
        355                 360                 365

Ala Asn Asn Arg Val Gly Leu Ala Lys Ala Ile
    370                 375

<210> SEQ ID NO 7
<211> LENGTH: 4
<212> TYPE: PRT
<213> ORGANISM: Bos taurus

<400> SEQUENCE: 7

Met Arg Cys Leu
1

<210> SEQ ID NO 8
<211> LENGTH: 5
<212> TYPE: PRT
<213> ORGANISM: Bos taurus

<400> SEQUENCE: 8

Leu Ala Lys Ala Ile
1               5
```

```
<210> SEQ ID NO 9
<211> LENGTH: 37
<212> TYPE: PRT
<213> ORGANISM: Camelus sp.
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(36)
<223> OTHER INFORMATION: Any amino acid

<400> SEQUENCE: 9

Arg Xaa Xaa Xaa Xaa Xaa Xaa Asn Xaa Gly Xaa Xaa Arg Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Lys
        35

<210> SEQ ID NO 10
<211> LENGTH: 37
<212> TYPE: PRT
<213> ORGANISM: Bos taurus
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(36)
<223> OTHER INFORMATION: Any amino acid

<400> SEQUENCE: 10

Gln Xaa Xaa Xaa Xaa Xaa Xaa Asp Xaa Asp Xaa Xaa Ser Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Gln
        35
```